(12) United States Patent
Suzuki

(10) Patent No.: US 10,295,553 B2
(45) Date of Patent: May 21, 2019

(54) BLOOD ANALYZING METHOD AS WELL AS STAIN SOLUTION AND BLOOD ANALYZER USED FOR THE SAME

(71) Applicant: SYSMEX CORPORATION, Kobe-shi, Hyogo (JP)

(72) Inventor: Yuhgi Suzuki, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 227 days.

(21) Appl. No.: 15/242,739

(22) Filed: Aug. 22, 2016

(65) Prior Publication Data

US 2017/0059592 A1    Mar. 2, 2017

(30) Foreign Application Priority Data

Aug. 31, 2015   (JP) ................................. 2015-171431

(51) Int. Cl.
| | |
|---|---|
| *G01N 33/80* | (2006.01) |
| *G01N 21/64* | (2006.01) |
| *G01N 1/30* | (2006.01) |
| *G01N 33/569* | (2006.01) |

(52) U.S. Cl.
CPC .............. *G01N 33/80* (2013.01); *G01N 1/30* (2013.01); *G01N 21/6428* (2013.01); *G01N 33/56905* (2013.01); *G01N 2001/302* (2013.01); *G01N 2021/6439* (2013.01); *G01N 2201/0612* (2013.01); *G01N 2333/445* (2013.01); *G01N 2800/26* (2013.01); *Y02A 50/58* (2018.01)

(58) Field of Classification Search
CPC ............ G01N 33/56905; G01N 33/80; G01N 21/6428; G01N 1/30; G01N 2333/445; G01N 2201/0612; G01N 2021/6439; G01N 2001/302; G01N 2800/26
See application file for complete search history.

(56) References Cited

U.S. PATENT DOCUMENTS

2006/0223137 A1   10/2006   Yoshida et al.

FOREIGN PATENT DOCUMENTS

| EP | 2 293 062 A1 | 3/2011 |
|---|---|---|
| WO | 2013/183656 A1 | 12/2013 |

OTHER PUBLICATIONS

Jillian Howlin, et al., "TNK2 preserves epidermal growth factor receptor expression on the cell surface and enhances migration and invasion of human breast cancer cells", Breast Cancer Research, Apr. 24, 2008, vol. 10, No. 2, pp. 1-13.

*Primary Examiner* — Christopher Adam Hixson
(74) *Attorney, Agent, or Firm* — Sughrue Mion, PLLC

(57) ABSTRACT

Disclosed is a blood analyzing method including: a step of preparing a measurement sample from blood, a fluorescent dye represented by the following formula 1, and a diluent, a concentration of the fluorescent dye in the measurement sample being greater than or equal to 0.15 μM and smaller than or equal to 1.0 μM; a step of acquiring fluorescence information obtained by irradiating the measurement sample with light; and a step of detecting a red blood cell infected with a malaria parasite in the blood based on the fluorescence information.

[Chemical Formula 1]

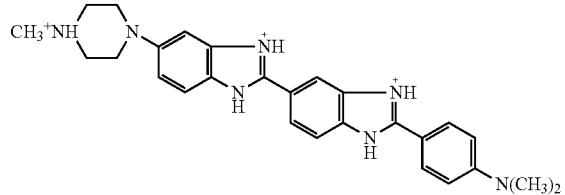

Formula 1

8 Claims, 19 Drawing Sheets

BLOOD ANALYZING METHOD AS WELL AS STAIN SOLUTION AND BLOOD ANALYZER USED FOR THE SAME

CROSS REFERENCE TO RELATED APPLICATIONS

This application claims priority from prior Japanese Patent Application No. 2015-171431, filed on Aug. 31, 2015, entitled "BLOOD ANALYZING METHOD AND STAIN SOLUTION AND BLOOD ANALYZER USED FOR THE SAME", the entire contents of which are incorporated herein by reference.

TECHNICAL FIELD

The present invention relates to a blood analyzing method as well as a stain solution and a blood analyzer used for the same.

BACKGROUND

U.S. Patent Application Publication No. 2006/0223137 discloses a reagent for partial lysis of a cell membrane of a red blood cell so as to enable a fluorescent dye to be transmitted while holding a malaria parasite inside the red blood cell. In the Examples, a description is made for detecting a malaria infected red blood cell using a measurement sample (concentration of Hoechst 34580: 1.80 µM) prepared by adding 2 µl of a dye solution (0.5 mg/ml), in which Hoechst 34580 as a fluorescent dye is dissolved with ethylene glycol, and 1 ml of the reagent for partial lysis of the cell membrane of the red blood cell to 20 µl of a specimen, and subjecting the measurement sample to a flow cytometer.

SUMMARY OF THE INVENTION

The scope of the present invention is defined solely by the appended claims, and is not affected to any degree by the statements within this summary.

However, in the method for detecting the malaria infected red blood cell described in U.S. Unexamined Patent Application Publication No. 2006/0223137, for example, malaria infected red blood cells and other particles may sometimes overlap in a specimen with high value of reticulocyte (RET), and the like. Furthermore, there is also a problem that discrimination between malaria infected red blood cells and malaria non-infected red blood cells is difficult in a specimen with low malaria infection rate. Thus, it has been desirable to further improve the separation capacity between the malaria infected red blood cells and the malaria non-infected red blood cells.

The present inventors have found that the separation capacity between the malaria infected red blood cells and the malaria non-infected red blood cells can be further improved by using Hoechst 34580 as a fluorescent dye not at high concentration but rather at low concentration, and have completed the present invention.

In other words, the present invention provides a blood analyzing method including: preparing a measurement sample from blood, a fluorescent dye represented by the following formula 1, and a diluent, a concentration of the fluorescent dye in the measurement sample being greater than or equal to 0.15 µM and smaller than or equal to 1.0 µM; acquiring fluorescence information obtained by irradiating the measurement sample with light; and detecting a red blood cell infected with a malaria parasite in the blood based on the fluorescence information.

[Chemical Formula 1]

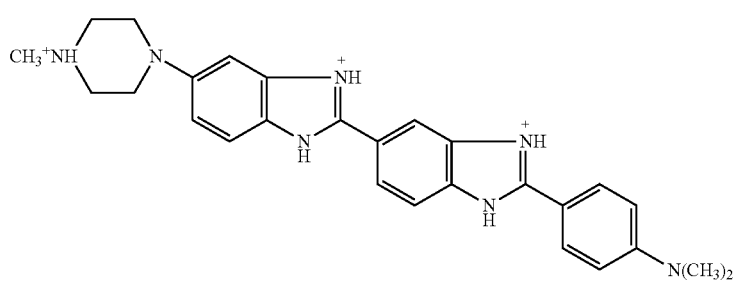

Formula 1

The present invention provides a stain solution for analyzing malaria comprising the fluorescent dye represented by the following formula 1, a concentration of the fluorescent dye in the stain solution being greater than or equal to 3 µM and smaller than or equal to 200 µM.

[Chemical Formula 2]

Formula 1

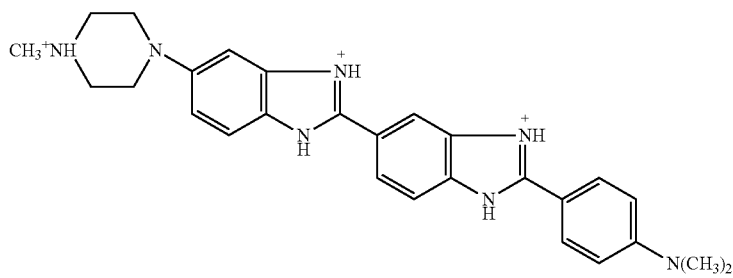

Furthermore, the present invention provides a blood analyzer including: a measurement sample preparing section that prepares a measurement sample from blood, a fluorescent dye represented by the following formula 1, and a diluent, a concentration of the fluorescent dye in the measurement sample being greater than or equal to 0.15 μM and smaller than or equal to 1.0 μM; a light source section that irradiates the measurement sample with light; a detecting section that acquires fluorescence information obtained from the measurement sample irradiated with light; and a control section that detects a red blood cell infected with a malaria parasite in the blood based on the fluorescence information.

[Chemical Formula 3]

Formula 1

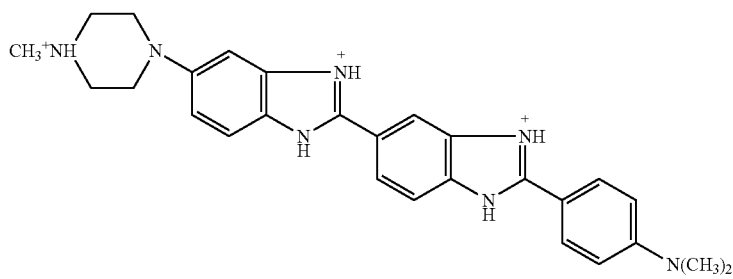

The present invention provides a method for detecting a malaria infected red blood cell at satisfactory detection accuracy.

DETAILED DESCRIPTION OF THE PREFERRED EMBODIMENTS

A blood analyzing method includes a step of preparing a measurement sample from blood, a fluorescent dye represented by the following formula 1, and a diluent, a concentration of the fluorescent dye in the measurement sample being greater than or equal to 0.15 µM and smaller than or equal to 1.0 µM.

Figure 3:
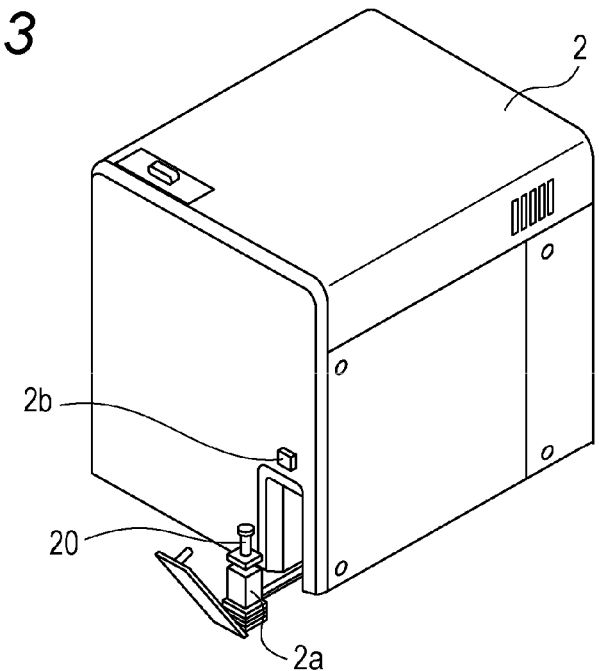
FIG. 3 is a perspective view showing a measurement unit of the blood analyzer according to one embodiment shown in FIG. 1.

In blood cell classification using the flow cytometry technique as described in U.S. Unexamined Patent Application Publication No. 2006/0223137, the particles to be stained are wholly shifted toward a high fluorescence intensity side by increasing the concentration of the fluorescent dye (e.g., FIG. 3 and the like in U.S. Unexamined Patent Application Publication No. 2006/0223137). Thus, in order to improve the separation capacity between a certain blood cell group and another blood cell group, it is usually typical for those skilled in the art to increase the concentration of the fluorescent dye.

The present inventors have attempted to improve the separation capacity using a fluorescent dye with higher concentration (18.0 µM) than that described in U.S. Unexamined Patent Application Publication No. 2006/0223137. However, contrary to the expectation, the fluorescence intensity of a malaria infected red blood cell did not rise (see FIG. 12 to be described later). On the contrary, the fluorescence intensity of a malaria non-infected red blood cell demonstrating a lower fluorescent intensity than the malaria infected red blood cell rose, which led to degradation in the separation capacity.

It is a surprising viewpoint found by the present inventors this time that the separation capacity between the malaria infected red blood cells and the malaria non-infected red blood cells can be further improved using Hoechst 34580 as the fluorescent dye at low concentration rather than at high concentration.

(Fluorescent Dye)

The fluorescent dye represented by the above formula 1 is well known to those skilled in the art as CAS number 911004-45-0, and is also referred to as Hoechst 34580. Such a fluorescent dye is a DNA selective fluorescent dye that stains DNA stronger than RNA. Such a fluorescent dye can, for example, be excited by a blue-violet laser light (wave-

[Chemical Formula 4]

Formula 1

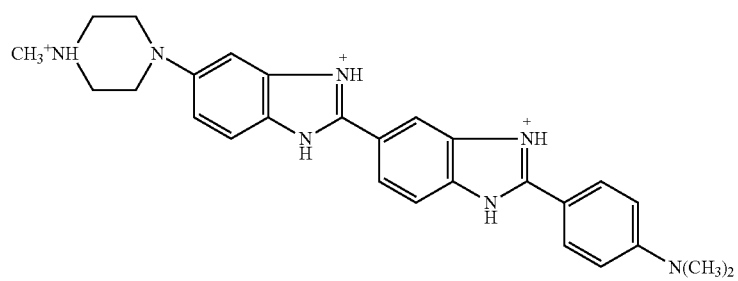

<Measurement Sample>

The measurement sample is a sample subjected to a flow cytometer to conduct measurement, and contains blood as a specimen as well as the fluorescent dye (Hoechst 34580) represented by the following formula 1 and the diluent. The lower limit of the concentration of the fluorescent dye in the measurement sample is 0.15 µM, preferably 0.16 µM, and more preferably 0.18 µM. The upper limit of the concentration of the fluorescent dye in the measurement sample is 1.0 µM, preferably 0.95 µM, and more preferably 0.89 µM. Specific numerical values of the concentration of the fluorescent dye in the measurement sample include, for example, 0.15, 0.18, 0.2, 0.25, 0.3, 0.35, 0.36, 0.4, 0.45, 0.5, 0.55, 0.6, 0.62, 0.65, 0.7, 0.75, 0.8, 0.85, 0.89, 0.9, 0.95, 1.0 (unit: µM).

length of about 405 nm). The above-described fluorescent dye may be synthesized according to a known method, or a commercially available product may be used.

The fluorescent dye exists in the form of ions in the solution. In the present specification, such a solution is also referred to as a malaria analyzing stain solution or a stain solution. A solvent of the stain solution is not particularly limited as long as the blood analysis is not hindered. The solvent is preferably ethylene glycol, diethylene glycol, polyethylene glycol, water, normal saline, lower alcohol (ethanol, etc.) with a carbon number of 1 to 6, and a mixture thereof, and more preferably, ethylene glycol. A counter ion is not particularly limited as long as the blood analysis is not hindered. The counter ion is preferably a halide ion, and more preferably, a chloride ion ($Cl^-$).

The lower limit of the concentration of the fluorescent dye in the stain solution is preferably 3 µM, more preferably 10 µM, and furthermore preferably 50 µM. The upper limit of the concentration of the fluorescent dye in the stain solution is preferably 200 µM, more preferably 180 µM, and furthermore preferably 150 µM. Specific numerical values of the concentration of the fluorescent dye in the stain solution include, for example, 3, 5, 10, 20, 30, 40, 50, 60, 70, 80, 90, 100, 110, 120, 130, 140, 150, 160, 170, 180, 190, 200 (unit: µM).

The values of the lower limit and upper limit of the concentration of the fluorescent dye in the stain solution are based on the fact that there is a limit in terms of accuracy management when the measurement sample as used in the present embodiment which is subjected to the blood analyzer is prepared. In other words, when the measurement sample as used in the present embodiment which is subjected to the blood analyzer is prepared, the volume of the stain solution that can be pipetted is generally greater than or equal to about 5 µL and smaller than or equal to about 50 µL. The volume of the diluent to be added to the stain solution in the blood analyzer is 1.0 mL, and hence the diluting magnification of the fluorescent dye when the measurement sample is prepared from the stain solution is about 20 times to about 200 times. When taking into consideration that the concentration of the fluorescent dye in the measurement sample is greater than or equal to 0.15 µM and smaller than or equal to 1.0 µM, the lower limit and upper limit of the concentration of the fluorescent dye in the stain solution are 3 µM and 200 µM, respectively. The volume of blood is very small so that it is ignored in the calculation of the lower limit and upper limit of the concentration described above.

The method for preparing the stain solution is not particularly limited, and the stain solution can be prepared according to a method known to those skilled in the art. For example, the stain solution can be prepared by mixing the above described fluorescent dye and the above described solvent. When the fluorescent dye and the solvent are mixed to prepare the stain solution, the mixture may be stirred. The stirring conditions such as stirring speed and stirring time can be appropriately set by those skilled in the art.

(Specimen Diluent)

The diluent contains a hemolytic agent that can solubilize red blood cells, and preferably, a surfactant. Examples of the surfactant include cationic surfactants such as lauryltrimethylammonium chloride, stearyltrimethylammonium chloride, myristyltrimethylammonium chloride and cetyltrimethylammonium chloride; anionic surfactants such as dodecyl sodium sulfate; ampholytic surfactants such as CHAPS; nonionic surfactants such as PBC-44, and a mixture thereof. The surfactant is preferably lauryltrimethylammonium chloride, stearyltrimethylammonium chloride, and PBC-44. More preferably, the hemolytic agent includes at least two types of surfactants having different dissolving powers with respect to cell membranes of red blood cells. Specific examples of the combination of such at least two types of surfactants include a combination of lauryltrimethylammonium chloride, stearyltrimethylammonium chloride and PBC-44; a combination of myristyltrimethylammonium chloride and cetyltrimethylammonium chloride; and the like, and preferably a combination of lauryltrimethylammonium chloride, stearyltrimethylammonium chloride and PBC-44.

The lower limit of the pH of the diluent is preferably 5.0, and more preferably 5.5. The upper limit of pH of the diluent is preferably 7.0, and more preferably 6.5. Specific numerical values of the pH of the diluent may be, for example, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 (no unit).

The lower limit of the osmotic pressure of the diluent with respect to red blood cells is preferably, 200 mOsm/kg·$H_2O$, and more preferably 220 mOsm/kg·$H_2O$. The upper limit of the osmotic pressure of the diluent with respect to red blood cells is preferably, 300 mOsm/kg·$H_2O$, and more preferably 280 mOsm/kg·$H_2O$. Specific numerical values of the osmotic pressure of the diluent with respect to red blood cells may be, for example, 200, 210, 220, 230, 240, 250, 260, 270, 280, 290, 300 (unit: mOsm/kg·$H_2O$).

When red blood cells contain a malaria infected red blood cell, a malaria parasite is inside the malaria infected red blood cell. The red blood cells in the measurement sample are reduced by the action of the hemolytic agent. The malaria infected red blood cell is reduced by the hemolytic agent while interiorly holding a malaria parasite.

(Blood)

Blood to be a specimen is not particularly limited as long it is collected from a living body having blood flowing therein. The living body may be human or animals other than human such as chicken, monkey, or the like, but is preferably human. The living body may be a specimen with high value of reticulocyte (RET) or a specimen with low malaria infection rate. The blood can be collected from the living body through a method known to those skilled in the art, for example, blood drawing.

The measurement sample may be diluted with a diluent for DC measurement on the assumption that the concentration of the fluorescent dye in the measurement sample is within a range of the lower limit and the upper limit. The diluent for DC measurement is not particularly limited as long as it is suited for blood analysis, and is preferably a cell pack manufactured by Sysmex Corporation. In the present embodiment, however, a measurement sample for malaria measurement is not preferably diluted with the diluent for DC measurement. As will be described later, in the present embodiment, the diluent for DC measurement can also be used as a sheath fluid for optical measurement and DC measurement.

In another embodiment, a malaria infected red blood cell rate is calculated based on the measurement of red blood cell count or red blood cell count, in addition to the detection of the malaria infected red blood cells or the measurement of malaria infected red blood cell count. In this case, a measurement sample for the measurement of the red blood cell count is prepared apart from the measurement sample for malaria measurement. The measurement sample for the measurement of the red blood cell count is preferably diluted with the diluent described above.

(Method for Preparing Measurement Sample)

The method for preparing the measurement sample is not particularly limited, and the measurement sample can be prepared in accordance with the method known to those skilled in the art. For example, the measurement sample can be prepared by mixing the blood to be a specimen, the fluorescent dye described above (preferably, stain solution containing fluorescent dye), and the diluent.

The lower limit of the preparing temperature of the measurement sample is preferably 20° C., and more preferably 39° C. The upper limit of the preparing temperature of the measurement sample is preferably 45° C., and more preferably 43° C.

The lower limit of the preparing time of the measurement sample is preferably 10 seconds, and more preferably 20 seconds. The upper limit of the preparing time of the measurement sample is preferably 60 seconds, and more preferably 30 seconds.

When mixing the blood, the fluorescent dye, and the diluent in the preparation of the measurement sample, the mixture may be stirred. The stirring conditions such as stirring speed and stirring time can be appropriately set by those skilled in the art. When the measurement sample contains the diluent for DC measurement, the measurement sample can be prepared similar to the method for preparing the measurement sample described above except that the diluent for DC measurement is further mixed in addition to the blood, the fluorescent dye, and the diluent.

The blood analyzing method includes a step of acquiring fluorescence information obtained by irradiating the measurement sample prepared in the above manner with light. The wavelength of the irradiated light is not particularly limited as long as it is a wavelength that can excite the fluorescent dye represented by the above formula 1. The wavelength region of the irradiated light is, for example, greater than or equal to 375 nm and smaller than or equal to 420 nm. The intensity of the irradiated light can be appropriately set by those skilled in the art.

In the acquiring step, scattered light information may be acquired which is obtained by irradiating the measurement sample prepared in the above manner with light.

The method for acquiring the scattered light information and the fluorescence information is not particularly limited as long as information that contributes to blood analysis can be provided. The method for acquiring the scattered light information and the fluorescence information is preferably the flow cytometry technique. The scattered light information and the fluorescence information can be acquired using a general purpose flow cytometer. In the present embodiment, the scattered light information and the fluorescence information can be acquired using a flow cytometer built in a blood analyzer 1 described later.

The blood analyzing method includes a step of detecting a red blood cell infected with a malaria parasite in the blood based on the fluorescence information and arbitrarily the scattered light information acquired as above. The method for detecting a red blood cell infected with a malaria parasite is not particularly limited. The detection method is preferably a method that uses a computer program capable of analyzing forward scattered light information and side fluorescence information obtained by the flow cytometry technique.

Figure 1:
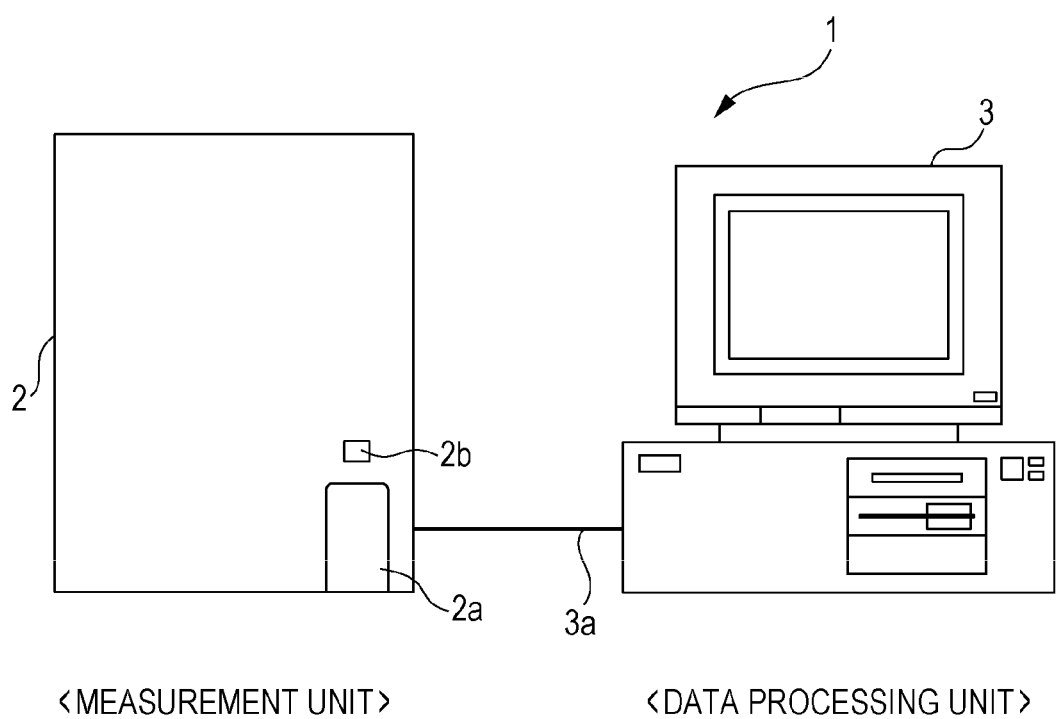
FIG. 1 is a front view showing a schematic configuration of a blood analyzer according to one embodiment of the present invention.

The step of acquiring the scattered light information and the fluorescence information, and the step of detecting a red blood cell infected with a malaria parasite can be conducted successively by using a blood analyzer shown in FIG. 1.

In the present embodiment, the red blood cell infected with the malaria parasite is detected using the computer program built in the blood analyzer shown in FIG. 1. More specifically, using the computer program described above, the forward scattered light information and the fluorescence information are plotted to create a scattergram, and the components in the blood to be a specimen are classified into three groups of a malaria infected red blood cell, a malaria non-infected red blood cell, and a white blood cell. In the present embodiment, the malaria infected red blood cell and the malaria non-infected red blood cell can be satisfactorily separated on the scattergram by using the fluorescence dye represented by the above formula 1 at a predetermined concentration.

The blood analyzer used in the present embodiment may conduct not only the detection of the malaria infected red blood cell, but also other blood analyses. For example, classification of white blood cells to finer groups (e.g., lymphocyte, acidocyte, etc.), the measurement of red blood cell count as well as the amount of hemoglobin, and the like can be conducted using such a blood analyzer. Even cases where the detection of the malaria infected red blood cell is conducted simultaneously with other blood analyses including white blood cells classification, the measurement of red blood cell count and the amount of hemoglobin, and the like also fall within the scope of the present disclosure.

The scope of the present disclosure also includes the measurement sample as it is. In other words, the present disclosure provides a measurement sample containing blood, a fluorescent dye represented by the following formula 1, and a diluent, the fluorescent dye having a concentration greater than or equal to 0.15 µM and smaller than or equal to 1.0 µM.

[Chemical Formula 5]

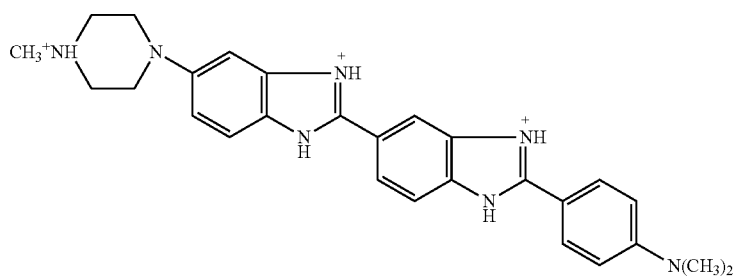

Formula 1

The blood, the fluorescent dye, the stain solution, the diluent, the preparing method, and the like are as described above. As described above, the measurement sample may be diluted with a diluent for DC measurement on the assumption that the concentration of the fluorescent dye is within the range of the lower limit and the upper limit. The diluent for DC measurement is as described above.

The scope of the present disclosure also encompasses the method for preparing the measurement sample. In other words, the present disclosure provides a method for preparing a measurement sample, the method including a step of preparing a measurement sample from blood, a fluorescent dye represented by the above formula 1, and a diluent, the measurement sample containing the fluorescent dye represented by the above formula 1 and having a concentration of the fluorescent dye of greater than or equal to 0.15 µM and smaller than or equal to 1.0 µM. The blood, the fluorescent dye, the stain solution, the diluent, the preparing method, and the like are as described above.

The scope of the present disclosure also encompasses the use of a measurement sample for blood analysis. In other words, the present disclosure provides the use for blood analysis of a measurement sample containing blood, a fluorescent dye represented by the above formula 1, and a diluent, the fluorescent dye having a concentration of greater than or equal to 0.15 µM and smaller than or equal to 1.0 µM. The blood, the fluorescent dye, the stain solution, the diluent, the preparing method, and the like are as described above. As described above, the measurement sample may be diluted with a diluent for DC measurement on the assumption that the concentration of the fluorescent dye is within the range of the lower limit and the upper limit. The diluent for DC measurement is as described above.

The scope of the present disclosure also encompasses the malaria analyzing stain solution as it is. In other words, the present disclosure provides a malaria analyzing stain solution containing a fluorescent dye represented by the above formula 1, the fluorescent dye having a concentration of greater than or equal to 3 µM and smaller than or equal to 200 µM. The fluorescent dye, the solvent, the preparing method, and the like are as described above.

The scope of the present disclosure also encompasses a method for preparing the malaria analyzing stain solution. In other words, the present disclosure provides a method for preparing a malaria analyzing stain solution, the method including a step of preparing a stain solution from a fluorescent dye represented by the above formula 1 and a solvent, the malaria analyzing stain solution containing the fluorescent dye represented by the above formula 1, and the fluorescent dye having a concentration of greater than or equal to 3 µM and smaller than or equal to 200 µM. The fluorescent dye, the solvent, the preparing conditions, and the like are as described above.

The scope of the present disclosure also encompasses the use of a malaria analyzing stain solution for blood analysis. In other words, the present disclosure provides the use for blood analysis of a malaria analyzing stain solution containing a fluorescent dye represented by the above formula 1, the fluorescent dye having a concentration of greater than or equal to 3 µM and smaller than or equal to 200 µM. The fluorescent dye, the solvent, the preparing method, and the like are as described above.

The scope of the present disclosure also encompasses a device for conducting the blood analyzing method. In other words, the present disclosure provides a blood analyzer including: a measurement sample preparing section that prepares a measurement sample from blood, a fluorescent dye represented by the above formula 1, and a diluent, the fluorescent dye having a concentration of greater than or equal to 0.15 µM and smaller than or equal to 1.0 µM; a light source section that irradiates the measurement sample with light; a detecting section that acquires fluorescence information obtained from the measurement sample irradiated with light; and a control section that detects a red blood cell infected with a malaria parasite in the blood based on the fluorescence information.

The detecting section may be configured to further acquire scattered light information obtained by irradiating the measurement sample with light. The control section may be configured to detect a red blood cell infected with a malaria parasite in the blood based on the scattered light information.

Hereinafter, embodiments of the blood analyzer will be described based on the drawings. First, a configuration of a blood analyzer 1 serving as one embodiment will be described with reference to FIGS. 1 to 10.

As shown in FIG. 1, a blood analyzer 1 according to the present embodiment is an apparatus used for blood examination, and is mainly configured by a measurement unit 2 and a data processing unit 3. The blood analyzer 1 is installed, for example in a facility of a medical institution such as a hospital or a pathology laboratory facility. In the blood analyzer 1, a predetermined measurement is conducted for components contained in blood by the measurement unit 2, and the measurement data thereof is received by the data processing unit 3 to conduct an analyzing process. The measurement unit 2 and the data processing unit 3 are connected by a data transfer cable 3a so that data can be communicated with each other. The measurement unit 2 and the data processing unit 3 may be configured to be directly connected by the data transfer cable 3a, or may be connected, for example, via a communication network such as a dedicated line using a telephone line, LAN, or Internet.

Figure 2:
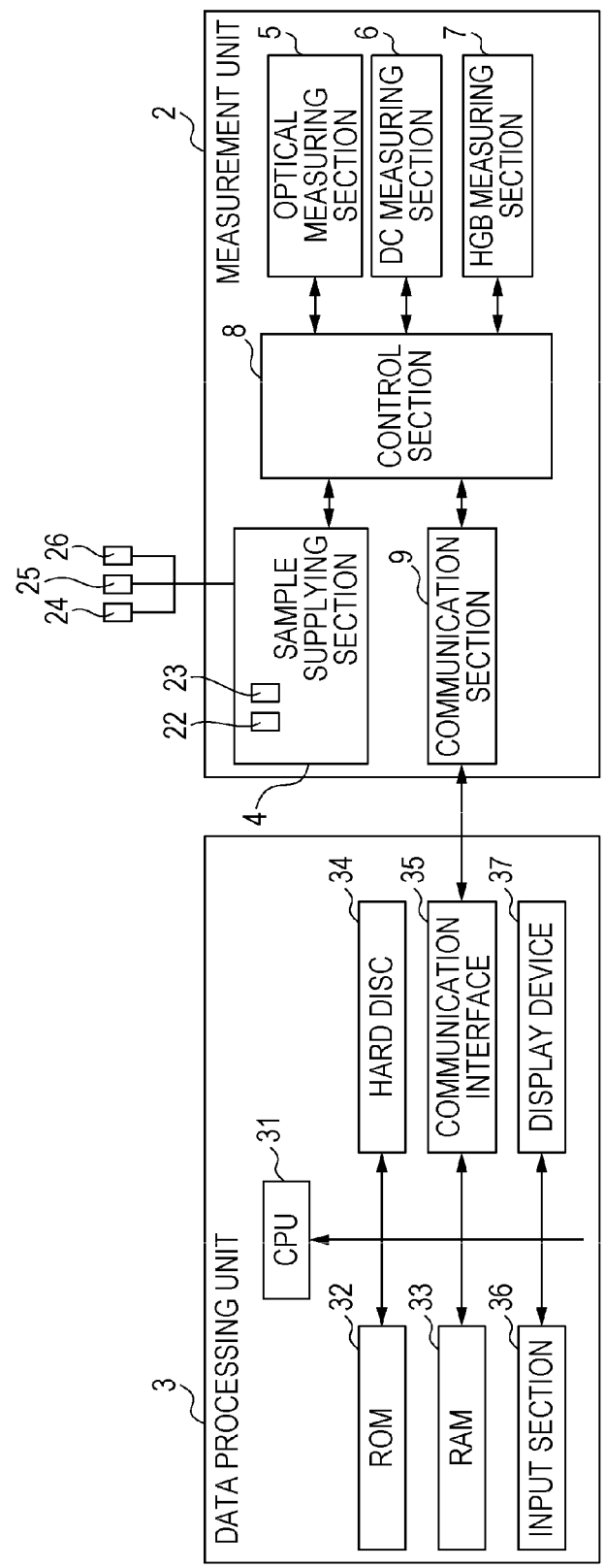
FIG. 2 is a block diagram showing a configuration of a blood analyzer according to one embodiment shown in FIG. 1.

As shown in FIG. 2, the measurement unit 2 includes a sample supplying section 4, an optical measuring section 5, a DC measuring section 6, an HGB measuring section 7, a control section 8, and a communication section 9. As shown in FIG. 3, a blood collecting tube setting portion 2a configured to be capable of setting a blood collecting tube 20 containing blood is provided at a lower right portion on the front surface of the measurement unit 2. The blood collecting tube setting portion 2a is configured to project out in a near side direction when a user presses a button switch 2b provided in the vicinity of the blood collecting tube portion 2a. The user can set the blood collecting tube 20 with the blood collecting tube setting portion 2a projecting out. After setting the blood collecting tube 20, the user again presses the button switch 2b so that the blood collecting tube setting portion 2a is configured to return into the measurement unit 2.

Figure 4:
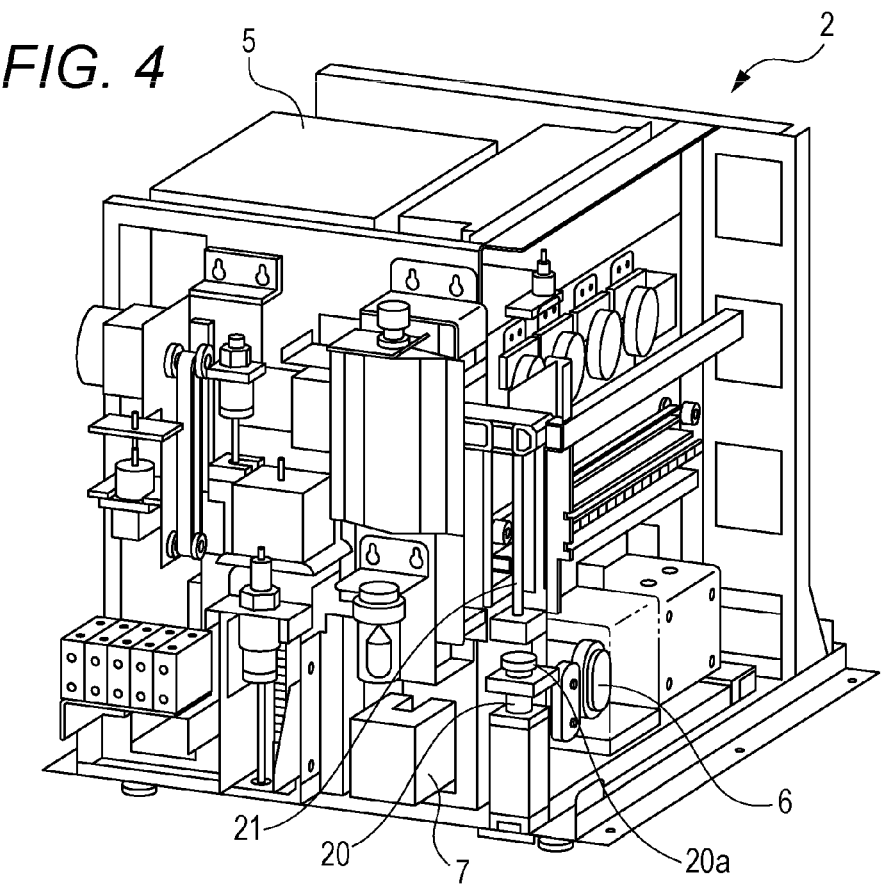
FIG. 4 is a perspective view showing an internal structure of the measurement unit of the blood analyzer according to one embodiment shown in FIG. 1.
Figure 5:
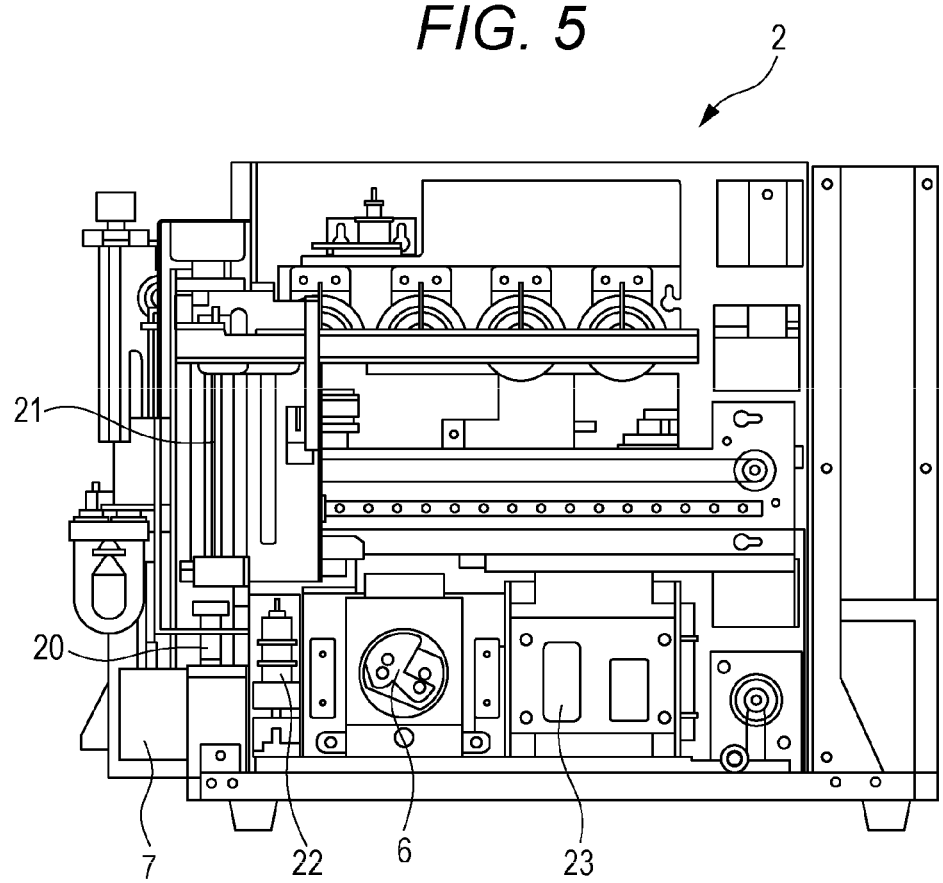
FIG. 5 is a side view showing the internal structure of the measurement unit of the blood analyzer according to one embodiment shown in FIG. 1.
Figure 6:
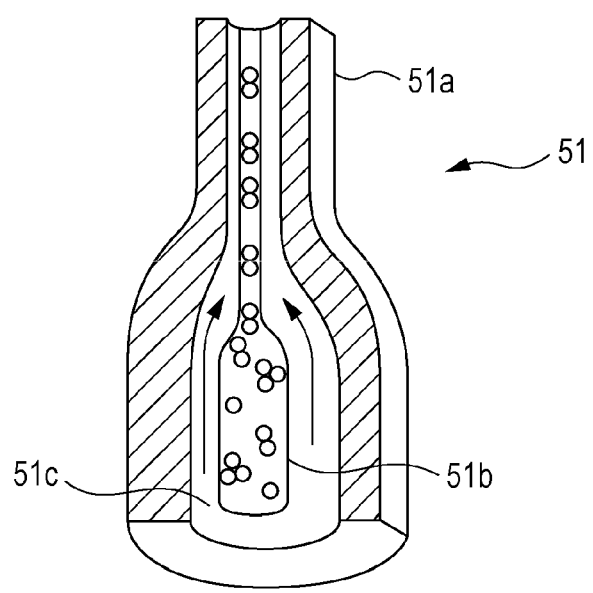
FIG. 6 is a perspective view schematically showing a configuration of a flow cell provided in the measurement unit of the blood analyzer according to one embodiment shown in FIG. 1.

As shown in FIGS. 4 and 5, a pipette 21 for suctioning blood and chambers 22, 23 (see FIG. 5) for mixing blood, fluorescent dye, and the like and preparing a measurement sample are provided inside the measurement unit 2. The pipette 21 is formed into a tubular shape extending in an up and down direction, where a distal end is sharply pointed. The pipette 21 is coupled to a syringe pump (not shown), and is configured to suction and discharge liquid in a predetermined amount by the operation of the syringe pump. The pipette 21 is connected to a moving mechanism, and is configured to be movable in the up and down direction and the front and back direction. The pipette 21 is configured to suction blood contained in the blood collecting tube 20 by perforating a sharp distal end into a rubber cap 20a for sealing the blood collecting tube 20. The pipette 21 is configured to be moved to a predetermined position by the moving mechanism after suctioning the blood to supply the blood into the chamber 22 or 23. In the present embodiment, an aspect of including two chambers has been described, but the chamber provided in the blood analyzer may be one or two or more.

The sample supplying section 4 is a fluid unit including the chambers 22 and 23, a plurality of electromagnetic valves, a diaphragm pump, and the like. The chambers 22 and 23 are provided to prepare the measurement sample. A reagent container is connected to the fluid unit configured by the sample supplying section 4. Specifically, a DC measurement diluent container 24 for containing a diluent for DC measurement, a diluent container 25 for containing a diluent, and a stain solution container 26 for containing a stain solution used in the measurement sample for malaria detection are connected to the fluid unit. The diluent for DC measurement, the diluent, and the stain solution thus can be supplied to the chamber 22 or 23. The diluent for DC measurement may or may not be supplied to the chamber 22 or 23, as necessary.

Figure 7:
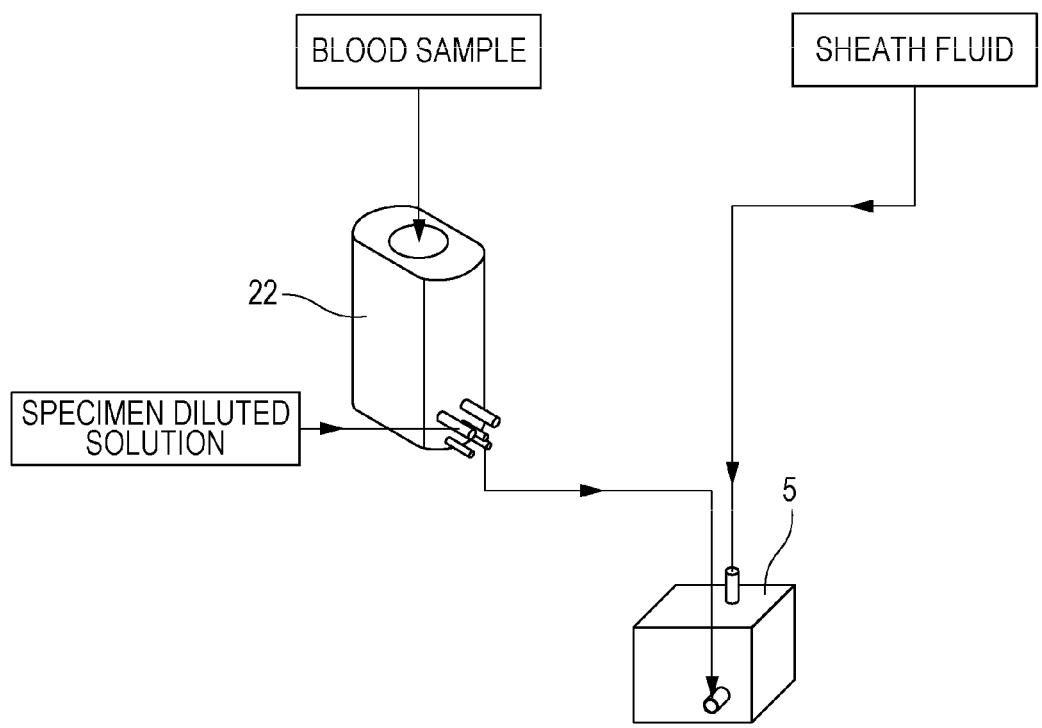
FIG. 7 is a schematic view showing a configuration of an optical measuring section as well as a chamber that supplies a fluorescent dye (stain solution) and a diluent to the optical measuring section provided in the measurement unit of the blood analyzer according to one embodiment shown in FIG. 1.
Figure 8:
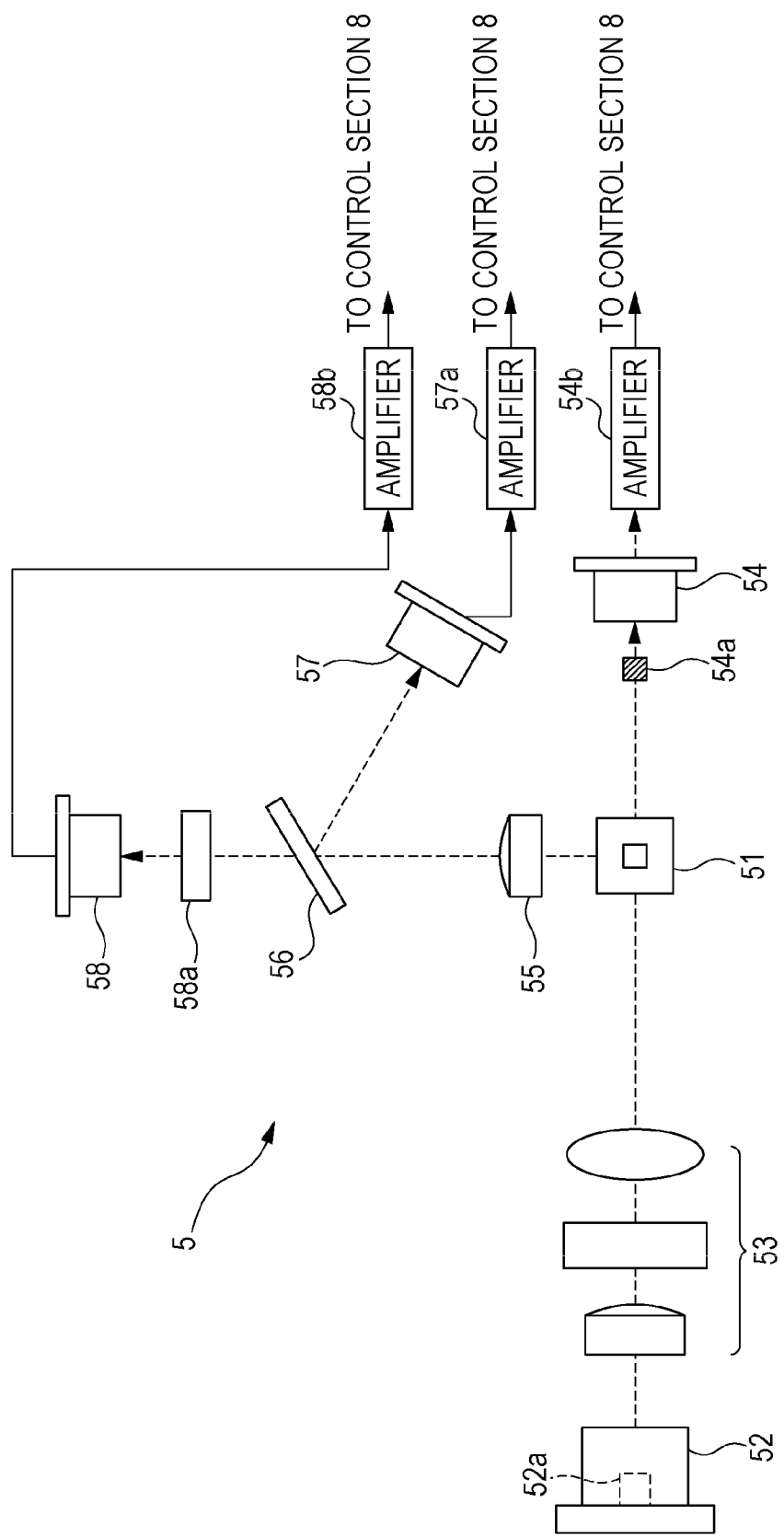
FIG. 8 is a schematic view showing a configuration of the optical measuring section provided in the measurement unit of the blood analyzer according to one embodiment shown in FIG. 1.

The optical measuring section 5 is an optical flow cytometer, and is provided to conduct malaria infected red blood cell detection (hereinafter referred to as malaria detection) with the flow cytometry technique using a semiconductor laser light. The optical measuring section 5 includes a flow cell 51 (see FIG. 6) that forms a liquid flow of the measurement sample. The flow cell 51 is formed into a tubular shape with a material such as quartz, glass, synthetic resin, and the like having translucency, where the interior is a flow path in which the measurement sample and the diluent for DC measurement serving as a sheath fluid flow. An orifice 51a in which an internal space is narrowed to be thinner than other portions is provided in the flow cell 51. The vicinity of an entry of the orifice 51a has a double tube structure, where the inner side tube portion is a sample nozzle 51b, and the measurement sample prepared in the chamber 22, and the like is supplied through the sample nozzle 51b (FIG. 7). A space on the outer side of the sample nozzle 51b is a flow path 51c where the diluent for DC measurement serving as the sheath fluid flows, and the diluent for DC measurement serving as the sheath fluid passes the flow path 51c to be introduced to the orifice 51a. The diluent for DC measurement serving as the sheath fluid supplied to the flow cell 51 as described above flows so as to surround the measurement sample discharged from the sample nozzle 51b. The flow of the measurement sample is narrowed by the orifice 51a, and particles such as white blood cells and red blood cells contained in the measurement sample are surrounded by the diluent for DC measurement serving as the sheath fluid and pass through the orifice 51a one by one.

A semiconductor laser light source 52 is disposed in the optical measuring section 5 to emit laser light toward the orifice 51a of the flow cell 51. The semiconductor laser light source 52 includes a blue-violet semiconductor laser element 52a, and is configured so as to be capable of emitting blue violet laser light having a wavelength of about 405 nm. An irradiation lens system 53 including a plurality of lenses is disposed between the semiconductor laser light source 52 and the flow cell 51. A parallel beam emitted from the semiconductor laser light source 52 is converged at a beam spot by the irradiation lens system 53. A beam stopper 54a is provided on an optical axis linearly extending from the semiconductor laser light source 52 so as to face the irradiation lens system 53 with the flow cell 51 interposed therebetween, and the beam stopper 54a is configured to shield direct light from the semiconductor laser light source 52.

A photodiode 54 is disposed on an optical axis on a further downstream side of the beam stopper 54a. The photodiode 54 is configured to receive scattered light of laser light generated by the measurement sample flowing through the flow cell 51. Specifically, the direct light of the semiconductor laser light source 52 among light advancing along the optical axis linearly extending from the semiconductor laser light source 52 is shielded by the beam stopper 54a, so that the photodiode 54 is configured to receive only scattered light (hereinafter referred to as forward scattered light) basically advancing along the optical axis direction. The forward scattered light emitted from the flow cell 51 is subjected to photoelectric conversion by the photodiode 54, and electrical signals (hereinafter referred to as forward scattered light signals) generated by this conversion are transmitted to an amplifier 54b. The amplifier 54b is configured to amplify the transmitted forward scattered light signals and output the amplified forward scattered light signals to a control section 8. The gain (amplification rate), the light receiving sensitivity, and the like of the light signals can be appropriately set and changed by those skilled in the art. When referring to changing the gain, this means changing the gain of the amplifier 54b and/or 58b when acquiring the light information.

A side collective lens 55 is disposed at a side of the flow cell 51, in a direction perpendicular to the optical axis extending linearly from the semiconductor laser light source 52 to the photodiode 54, and this side collective lens 55 is configured to collect lateral light (light emitted in a direction intersecting with the aforementioned optical axis) generated when emitting laser light to red blood cells passing through the flow cell 51. A dichroic mirror 56 is provided on a downstream side of the side collective lens 55, and the dichroic mirror 56 is configured to divide signal light transmitted from the side collective lens 55 into a scattered light component and a fluorescent light component. A side scattered light photoreceptor photodiode 57 is provided at a side (a direction intersecting with a direction of an optical axis connecting the side collective lens 55 and the dichroic mirror 56) of the dichroic mirror 56, and an optical filter 58a and an avalanche photodiode 58 are provided on an optical axis on a downstream side of the dichroic mirror 56. The side scattered light component separated by the dichroic mirror 56 is subjected to photoelectric conversion by the photodiode 57, and electrical signals (hereinafter referred to as side scattered light signals) generated by this conversion are transmitted to an amplifier 57a. The amplifier 57a is configured to amplify the transmitted side scattered light signals and output the amplified side scattered light signals to the control portion 8. The gain (amplification rate), the light receiving sensitivity, and the like of the light signals can be appropriately set and changed by those skilled in the art.

The side scattered light information obtained via the photodiode 57 and the amplifier 57a is not used in the malaria detection of the present embodiment, and thus is not essential in the configuration of the blood analyzer, but the flow cytometer equipped with the photodiode 57 and the amplifier 57a is more common. The side scattered light information obtained via the photodiode 57 and the amplifier 57a may be used when the measurement of red blood cell count, measurement of the amount of hemoglobin, and the like are conducted in addition to the malaria detection.

The side fluorescent light component is subjected to wavelength selection by the optical filter 58a, and to subsequent photoelectric conversion by the avalanche photodiode 58, and electrical signals (side fluorescent light signals) generated by this are transmitted to an amplifier 58b. The amplifier 58b is configured to amplify the transmitted side fluorescent light signals and output the amplified side fluorescent light signals to the control portion 8. The gain (amplification rate), the light receiving sensitivity, and the like of the light signals can be appropriately set and changed by those skilled in the art.

Figure 9:
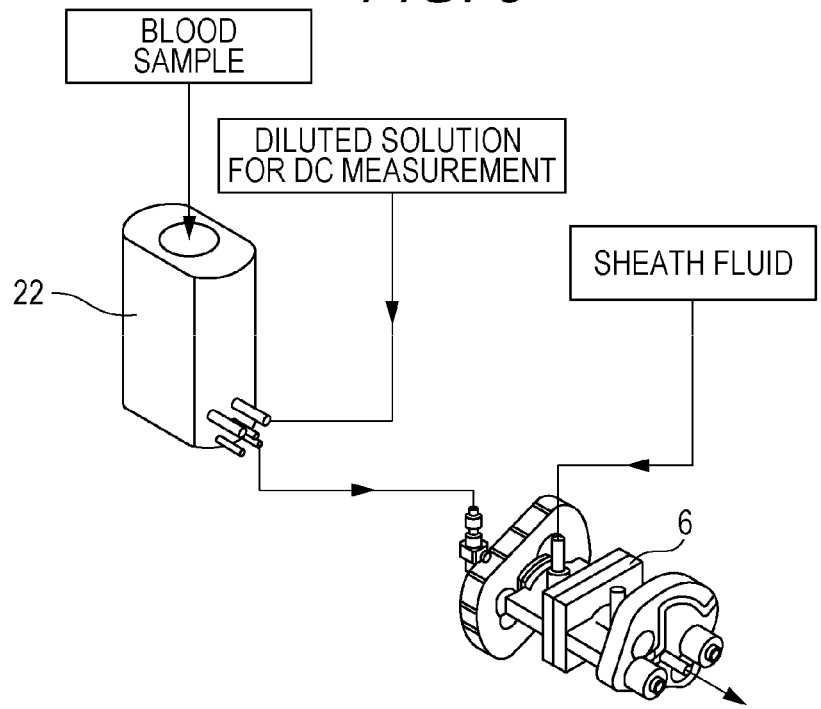
FIG. 9 is a perspective view schematically showing a configuration of a DC measuring section provided in the measurement unit of the blood analyzer according to one embodiment shown in FIG. 1.

The DC measuring section 6 is configured to be capable of measuring red blood cell count (RBC) and a platelet count (PLT) by a sheath flow DC detection method. The DC measuring section 6 is configured to be capable of acquiring measurement data for calculating a hematocrit value (HCT) by a red-blood-cell pulse height detection method. The DC measuring section 6 has a flow cell, and the measurement sample is transferred from the chamber 22 to the flow cell. For example, a measurement sample prepared by mixing blood and the diluent for DC measurement in the chamber 22, along with the diluent for DC measurement serving as the sheath fluid, is transferred from the sample supplying section 4 to the flow cell, as shown in FIG. 9. A fluid flow in a state where the measurement sample is surrounded by the diluent for DC measurement serving as the sheath fluid is formed in the flow cell.

The DC measuring section 6 is not used in the malaria detection of the present embodiment, and thus is not essential in the configuration of the blood analyzer, but a blood analyzer equipped with the DC measuring section 6 is more common. In particular, the DC measuring section 6 is preferably included when the measurement of red blood cell count and the like are conducted, or when a malaria infection rate is calculated based on the red blood cell count, in addition to the malaria detection. The measurement sample is preferably diluted with the diluent for DC measurement, as shown in FIG. 9, when the red blood cell count is conducted using the DC measuring section 6.

Figure 10:
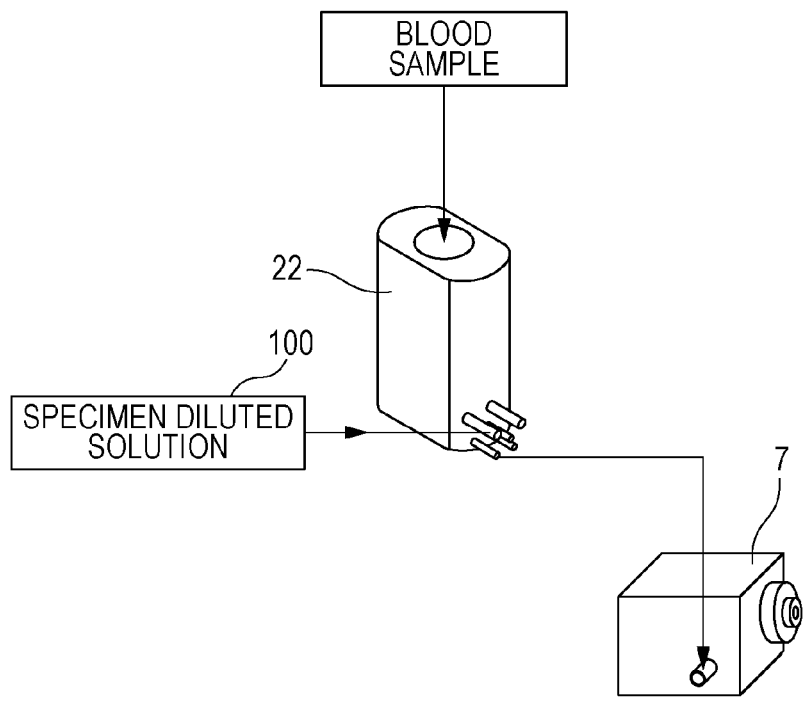
FIG. 10 is a perspective view schematically showing a configuration of an HGB measuring section provided in the measurement unit of the blood analyzer according to one embodiment shown in FIG. 1.

The HGB measuring section 7 is configured to measure the amount of hemoglobin (HGB) by the methemoglobin method. The HGB measuring section 7 has a cell storing a dilute sample, as shown in FIG. 10, and the measurement sample is transferred from the chamber 22 to this cell. The HGB measuring section 7 has a light-emitting diode emitting light having a wavelength of about 555 nm and is configured to measure absorbance of the measurement sample by emitting the light from the light-emitting diode to the measurement sample in the above cell.

The HGB measuring section 7 is not used in the malaria detection of the present embodiment, and thus is not essential in the configuration of the blood analyzer, but a blood analyzer equipped with the HGB measuring section 7 is more common. The HGB measuring section 7 can be used when the measurement of the amount of hemoglobin, and the like are conducted, in addition to the malaria detection.

The control section 8 is constituted by a CPU, a ROM, a RAM, etc. and configured to control an operation of each part of the measurement unit 2.

The communication section 9 is an RS-232C interface, a USB interface or an Ethernet (registered trademark) interface, for example and is configured to be capable of sending/receiving data to/from the data processing unit 3.

As shown in FIG. 2, the data processing unit 3 is constituted by a computer including a CPU 31, a ROM 32, a RAM 33, a hard disc 34, a communication interface 35, an input section 36 such as a keyboard and a mouse, and a display device 37. An operating system, and an application program for analyzing the measurement data received from the measurement unit 2 are installed on the hard disc 34 of the data processing unit 3.

In the present embodiment, the CPU 31 of the data processing unit 3 is configured to analyze the measurement data by executing the application program and prepare a scattergram using the forward scattered light signals and the side fluorescence signals.

The communication interface 35 is an RS-232C interface, a USB interface or an Ethernet (registered trademark) interface, for example and is configured to be capable of sending/receiving data to/from the measurement unit 2.

Figure 11:
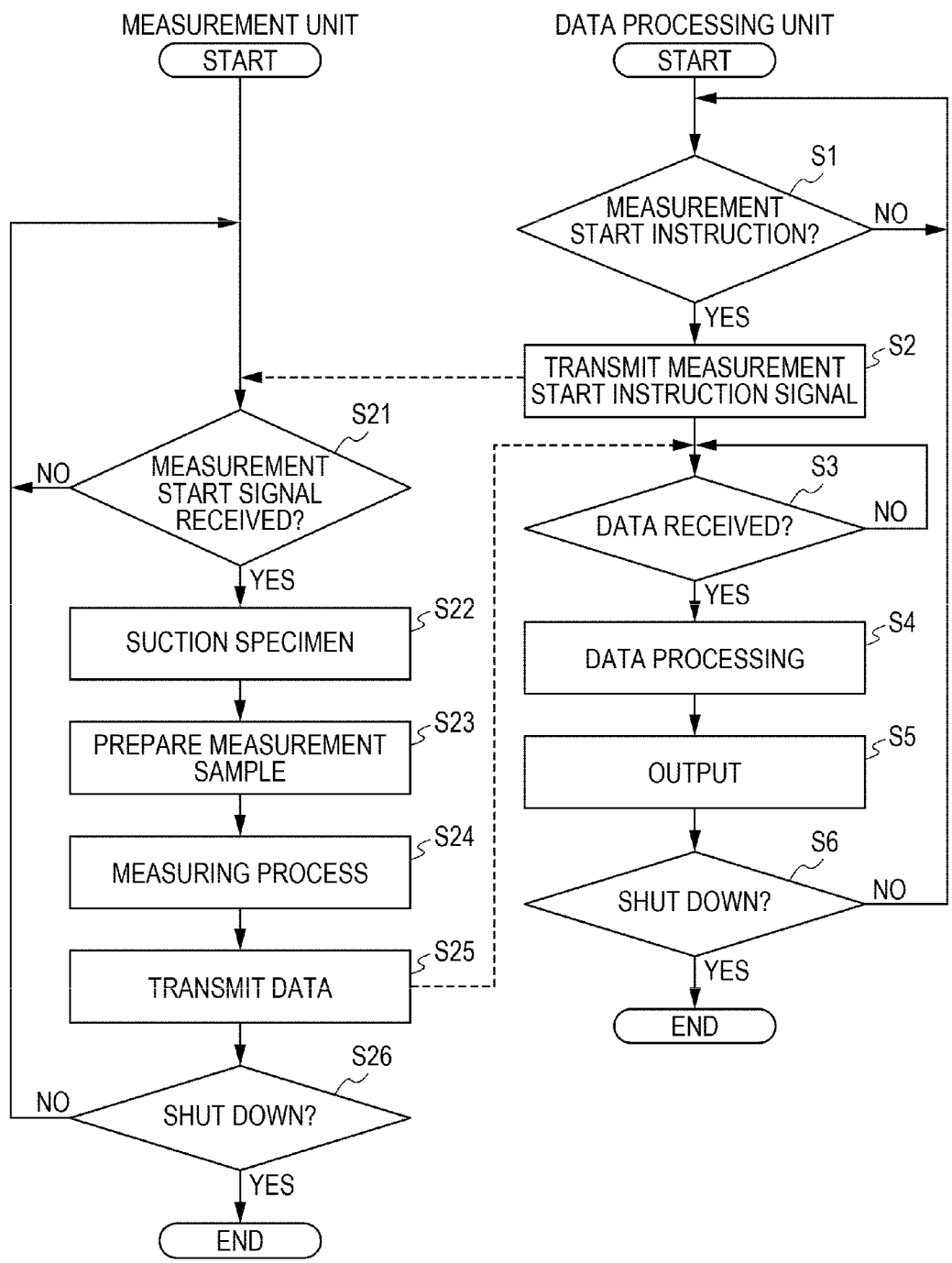
FIG. 11 is a flowchart showing a sample analyzing process in the blood analyzer according to one embodiment shown in FIG. 1.

Next, one embodiment of sample analyzing processing in the blood analyzer 1 will be described with reference to FIG. 11.

First, when the blood analyzer 1 is started, the application program or the like is initialized, and thereafter the CPU 31 of the data processing unit 3 determines whether or not a measurement starting instruction from a user has been received at step S1, and this determination is repeated until the instruction has been received. When the measurement starting instruction has been received, a measurement starting instruction signal is transmitted from the data processing unit 3 to the measurement unit 2 at step S2.

Then, the control section 8 of the measurement unit 2 determines whether or not the measurement starting instruction signal has been received at step S21, and this determination is repeated until the signal has been received. When the measurement unit 2 has received the measurement starting instruction signal, blood is suctioned from the blood collecting tube 20 set on the blood collecting tube setting portion 2a by the pipette 21 at step S22.

In step S23, a measurement sample is prepared by the sample supplying section 4. Specifically, blood, a stain solution including a fluorescent dye, a diluent, and as needed a diluent for DC measurement are supplied to the chamber 22 or 23 and mixed in the chamber 22 or 23 to prepare a measurement sample. The preparing conditions such as preparing temperature and stirring speed of the measurement sample can be set by warming and/or shaking the chamber 22 or 23. Thereafter, in step S24, the measurement sample in the chamber 22 or 23 is transferred to the optical measuring section 5 with the diluent for DC measurement serving as the sheath fluid, and malaria detection is conducted by the optical measuring section 5. When red blood cell detection is conducted in addition to the malaria detection, a measurement sample for the red blood cell detection is transferred to the DC measuring section 6 with the diluent for DC measurement serving as the sheath fluid, and the red blood cell detection is conducted by the DC measuring section 6. When hemoglobin (HGB) detection is conducted in addition to the malaria detection, a measurement sample for the hemoglobin detection is transferred to the HGB measuring section 7, and the hemoglobin detection is conducted by the HGB measuring section 7. In step S25, the measurement data measured in each detecting section is transmitted from the measurement unit 2 to the data processing unit 3.

In the data processing unit 3, whether or not the measurement data transmitted by the measurement unit 2 is received is determined in step S3, where such determination is repeated until the measurement data has been received. When the measurement data is received, malaria infected red blood cells are classified from a group other than the malaria infected red blood cells based on the measurement data by the malaria detection measured in step S24 by the CPU 31 in step S4. Specifically, the CPU 31 prepares a scattergram using the forward scattered light signals and the side fluorescence signals, and classifies the malaria infected red blood cells from the group other than the malaria infected red blood cells from the scattergram. More specifically, in the scattergram, red blood cells that are not infected with malaria appear in a region of small fluorescence intensity, whereas the malaria infected red blood cells appear in a region of relatively large fluorescence intensity. White blood cells appear in a region of both large fluorescence intensity and scattered light intensity due to the size and DNA amount thereof. The presence/absence of the malaria infection can be determined thereby. The measurement of the malaria infected red blood cell count, which could not be accomplished in the prior art, also becomes possible. When the red blood cell detection and/or the hemoglobin detection is conducted in step S24, the red blood cell count and/or the amount of hemoglobin can also be calculated based on the measurement data thereof. When both the detection of the malaria infected red blood cells and the detection of the red blood cells are conducted, the ratio of the malaria infected red blood cells can also be calculated based on the measurement data thereof. The ratio of the malaria infected red blood cells can be calculated by the following formula.

(Ratio of malaria infected red blood cells)=(number of malaria infected red blood cells)/(number of red blood cells)×100 (unit: %)    [Formula 1]

Thereafter, at step S6, the presence/absence of a shutdown instruction from the user is determined, and when the shutdown instruction has not been received, the CPU 31 moves to step S1. When the shutdown instruction has been received, an operation of the data processing unit 3 of the sample analysis processing in the blood analyzer 1 is terminated. In the measurement unit 2, after the measurement data is transmitted to the data processing unit 3 at step S25, whether or not a shutdown instruction from the user has been received is determined at step S26. When the shutdown instruction has not been received, the control section 8 moves to step S21. When the shutdown instruction has been received, an operation of the measurement unit 2 of the sample analysis processing in the blood analyzer 1 is terminated.

The present invention will be described in detail with reference to Examples, but the present invention is not limited to Examples.

EXAMPLES

Comparative Example 1

Twenty (20) μl of a stain solution and 1 ml of a diluent were added to 17 μl of whole human blood (ACD blood collection, type O) (manufactured by Golden West) added with a cultured malaria parasite (available from Research Institute for Microbial Diseases, Osaka University; hereinafter often referred to as "Malaria"), and mixed at 41° C. for 20 seconds to prepare a measurement sample. The stain solution and the diluent were prepared as below.

The diluent having the following composition was used.

TABLE 1

| | |
|---|---|
| Lauryltrimethylammonium chloride | 2.95 mM |
| Stearyltrimethylammonium chloride | 1.11 mM |
| PBC-44 (nonionic surfactant) | 2.90 mM |
| ADA | 20 mM (pH 6.1) |
| NaCl | Appropriate amount (277 mOsm) |
| Purified water | 1 L |

The stain solution in which a fluorescent dye (Hoechst 34580, Sigma-Aldrich) was dissolved in 1 ml of ethylene glycol was used. The concentration in the measurement sample when the following measurement sample is prepared using each stain solution is also shown in Table 2 below.

TABLE 2

| | HOECHST 34580 | Ethylene glycol | Concentration in measurement sample |
|---|---|---|---|
| Stain solution 1 | 50 μg | 1 ml | 1.80 μM |
| Stain solution 2 | 500 μg | 1 ml | 18.0 μM |

Using a flow cytometer having a blue light-emitting diode with 405 nm as a light source, forward scattered light signals and side fluorescence signals for the measurement sample prepared in the above manner were acquired, and a scattergram was prepared based on the obtained signals.

Figure 12:
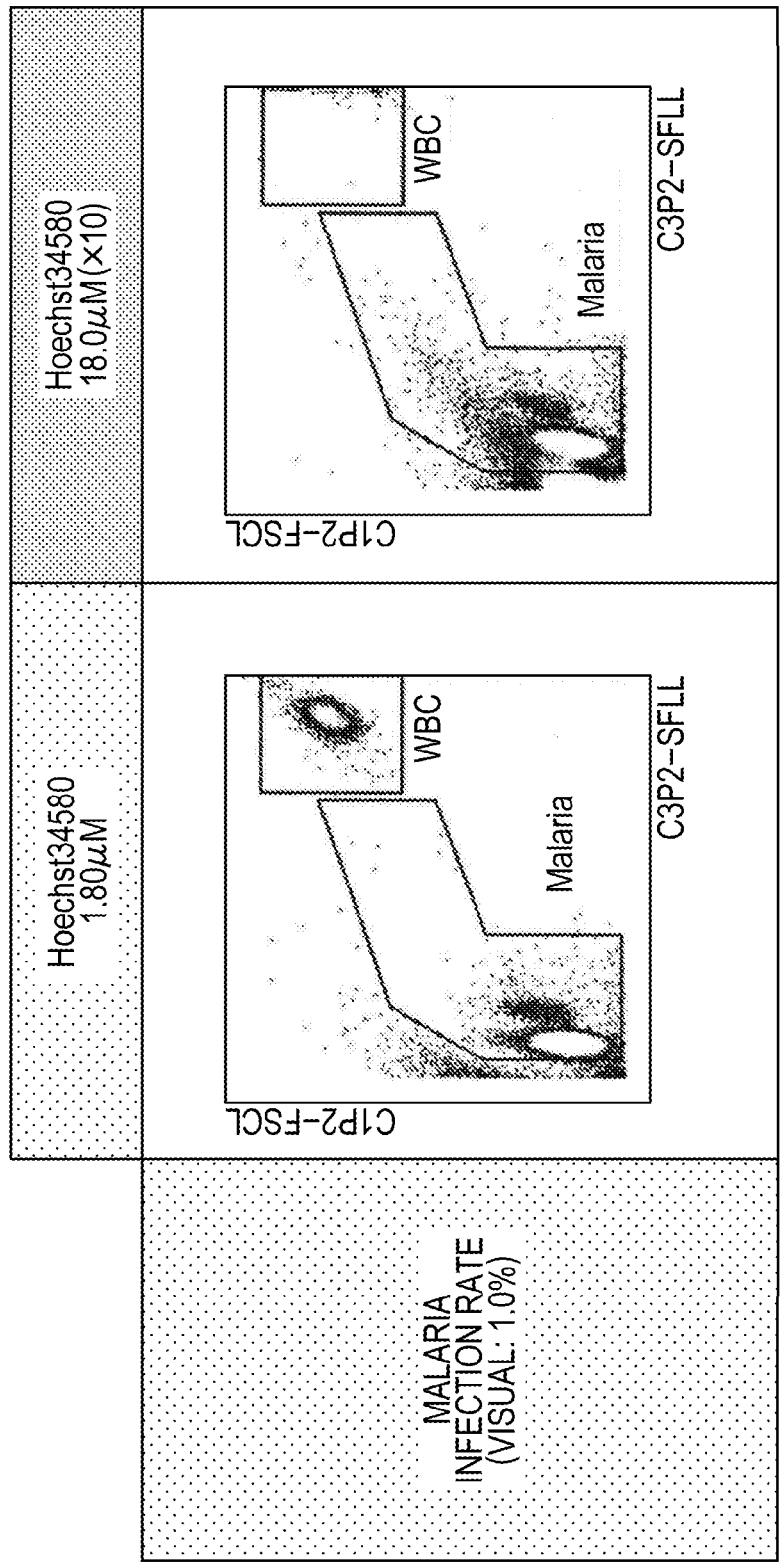
FIG. 12 is a scattergram when high concentration (18.0 μM) Hoechst 34580 was used.

The result of detecting the malaria infected red blood cells with the concentration of Hoechst 34580 in the measurement sample set to 18.0 μM, which is higher than 1.80 μM described in U.S. Unexamined Patent Application Publication No. 2006/0223137, is shown in FIG. 12. Since Hoechst 34580 is a nucleic acid stain dye, white blood cells and the malaria infected red blood cells containing nucleic acid are assumed to be stained more satisfactorily than red blood cells not containing nucleic acid. In FIG. 12, the group denoted "WBC" shown on the upper right is a group of white blood cells, the group denoted "Malaria" shown from the lower left toward the center is a group of malaria infected red blood cells, and the group shown on the left side of the malaria infected red blood cells is a group of malaria non-infected red blood cells. In FIG. 12, the fluorescence intensity of white blood cells (WBC) increased, as expected, and the appearing position thereof in the scattergram moved toward the right. However, an increase in the fluorescence intensity of the malaria infected red blood cells (Malaria) was small, and the separation capacity between the malaria infected red blood cells and the malaria non-infected red blood cells in which the fluorescence intensity increased by the influence of high concentration Hoechst 34580 degraded.

Example 1

An experiment was conducted in the same manner as in Comparative Example 1 using stain solutions each having the composition shown in Table 3 below.

TABLE 3

| | HOECHST 34580 | Ethylene glycol | Concentration in measurement sample |
|---|---|---|---|
| Stain solution 1 | 50 μg | 1 ml | 1.80 μM |
| Stain solution 3 | 12.5 μg | 1 ml | 0.45 μM |

Figure 13:
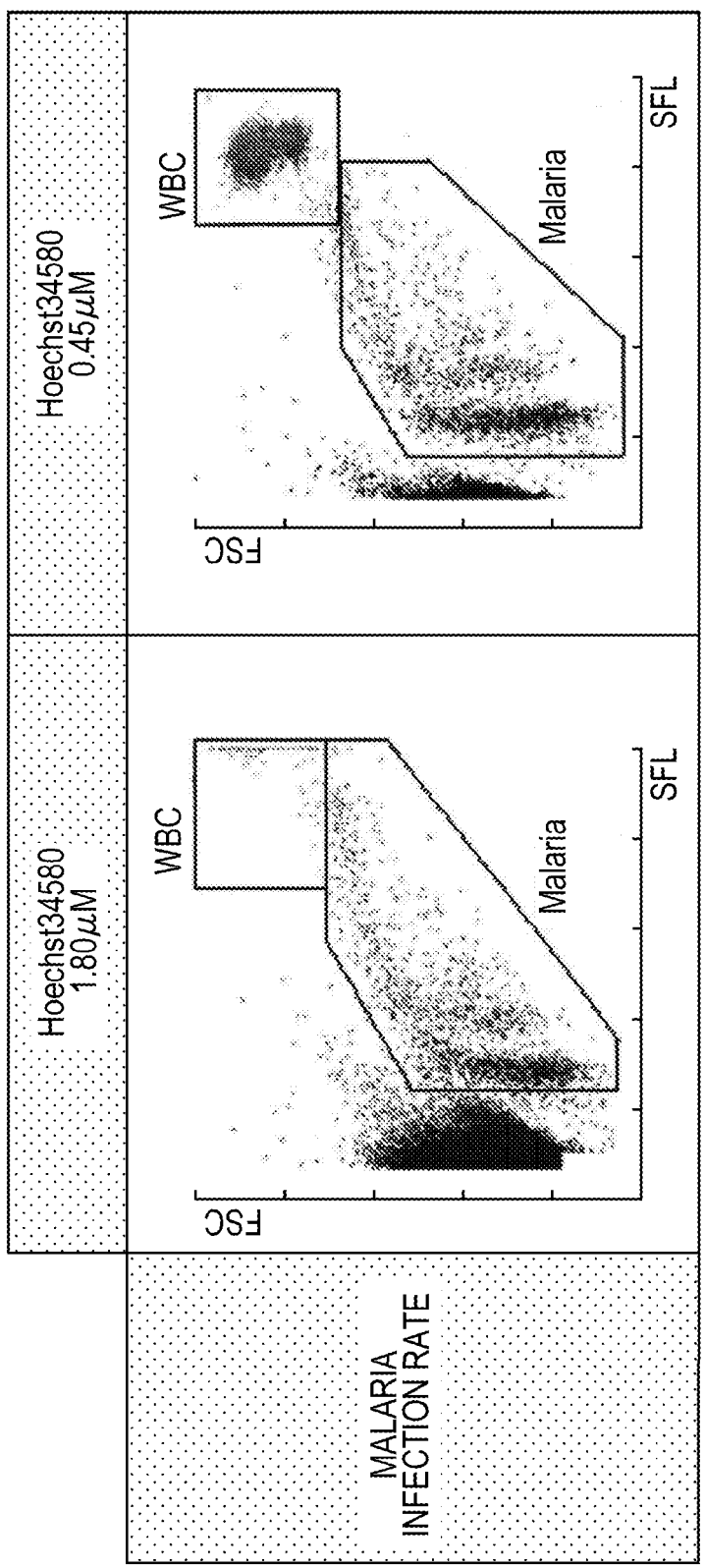
FIG. 13 is a scattergram when low concentration (0.45 μM) Hoechst 34580 was used.

The result of detecting the malaria infected red blood cells with the concentration of Hoechst 34580 in the measurement sample set to 0.45 μM, which is lower than 1.80 μM described in U.S. Unexamined Patent Application Publication No. 2006/0223137, is shown in FIG. 13. As apparent from FIG. 13, the separation capacity between the malaria infected red blood cells and the malaria non-infected red blood cells is improved by using the low concentration (0.45 μM) Hoechst 34580. In FIG. 13, and the like, the forward scattered light of the malaria non-infected red blood cell is greater than that of the malaria infected red blood cell. This is because the particles having a fluorescence intensity smaller than or equal to a predetermined threshold value are excluded so as to exclude normal red blood cells, and the normal blood cells that emit slight fluorescence such as RET, and the like that are still not excluded are displayed on the scattergram.

Figure 14:
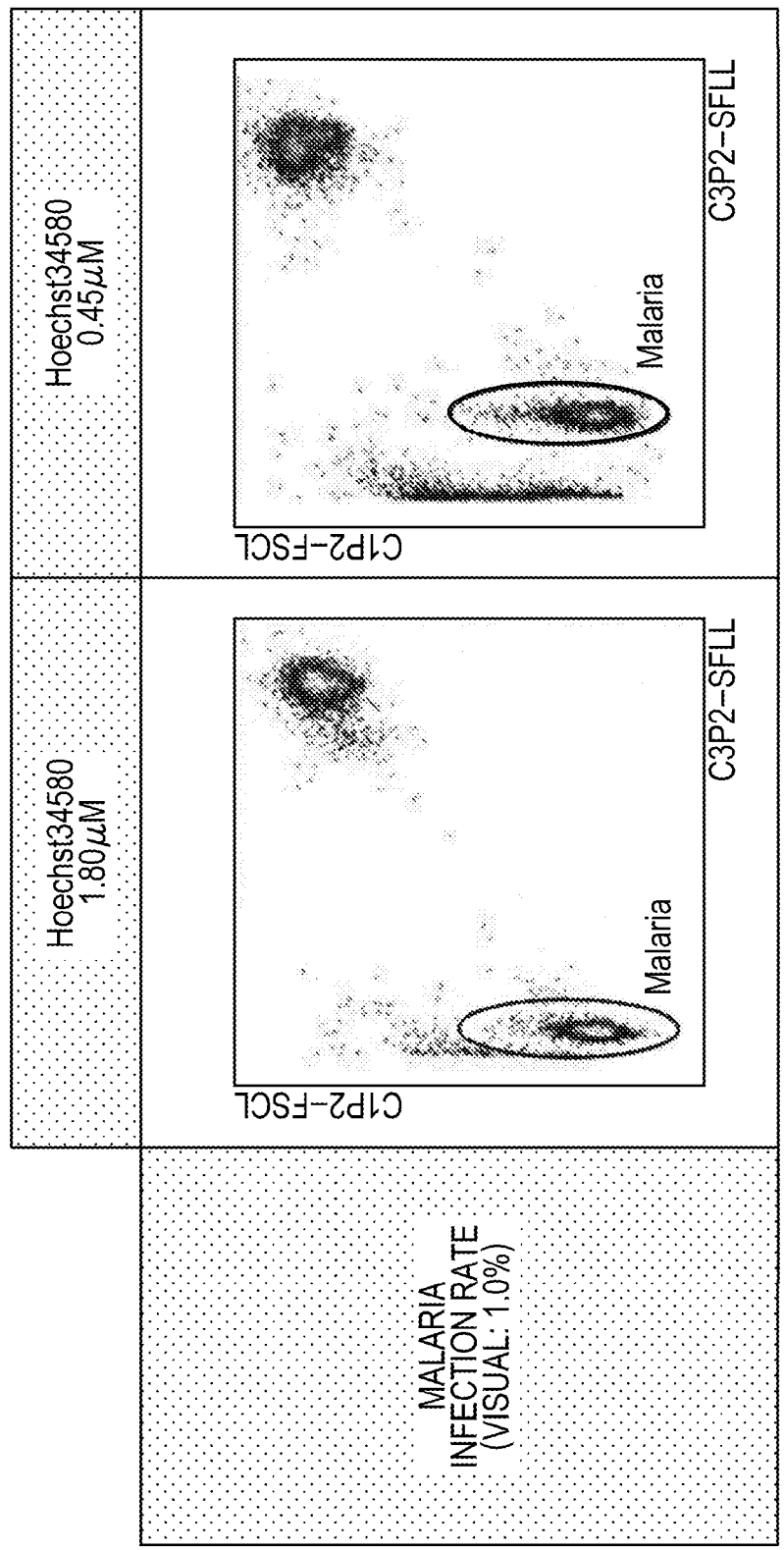
FIG. 14 is a scattergram (gain change) when low concentration (0.45 μM) Hoechst 34580 was used.

Next, a scattergram acquired when the gain is changed is shown in FIG. 14. In FIG. 14 as well, it was confirmed that the malaria infected red blood cell and the malaria non-infected red blood cell were satisfactorily separated when 0.45 μM of Hoechst 34580 was used. In FIG. 14, due to the change in the gain, the group of white blood cells was confirmed at substantially the same position as in the case of 0.45 µM in the scattergram when 1.80 µM of Hoechst 34580 was used. When the scattergram of 1.80 µM is compared with the scattergram of 0.45 µM, the separation of the malaria infected red blood cells from the malaria non-infected red blood cells is hard to confirm in the scattergram of 1.80 µM. In the scattergram of 0.45 µM, on the other hand, it can be confirmed that the malaria infected red blood cells and the malaria non-infected red blood cells are more satisfactorily separated. In Examples 2 and 3 below, a scattergram acquired when the gain is changed is shown for the scattergram when 1.80 µM of Hoechst 34580 was used.

Example 2

In place of the malaria infected whole human blood, blood collected from a patient infected with malaria and having high value of reticulocyte (RET) was used to conduct an experiment similar to Example 1.

Figure 15:
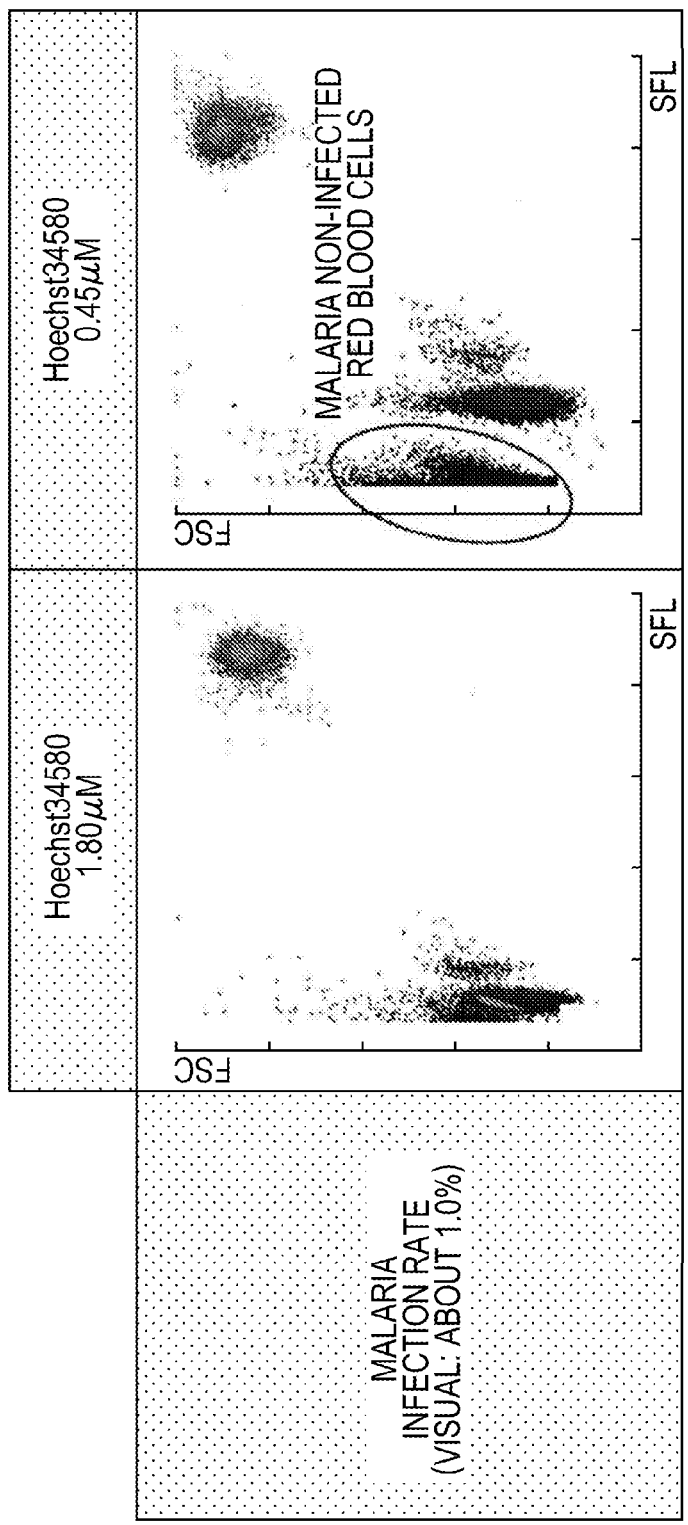
FIG. 15 is a scattergram when a specimen with high value of RET was used.

The result is shown in FIG. 15. As apparent from FIG. 15, the particles other than the malaria infected red blood cells and the malaria infected red blood cells overlap in 1.80 µM of Hoechst 34580 described in U.S. Unexamined Patent Application Publication No. 2006/0223137, but the separation capacity between the malaria infected red blood cells and the other particles is improved by using the low concentration (0.45 µM) Hoechst 34580.

Example 3

In place of the malaria infected whole human blood, blood collected from a patient with low malaria infection rate was used to conduct an experiment similar to Example 1.

Figure 16:
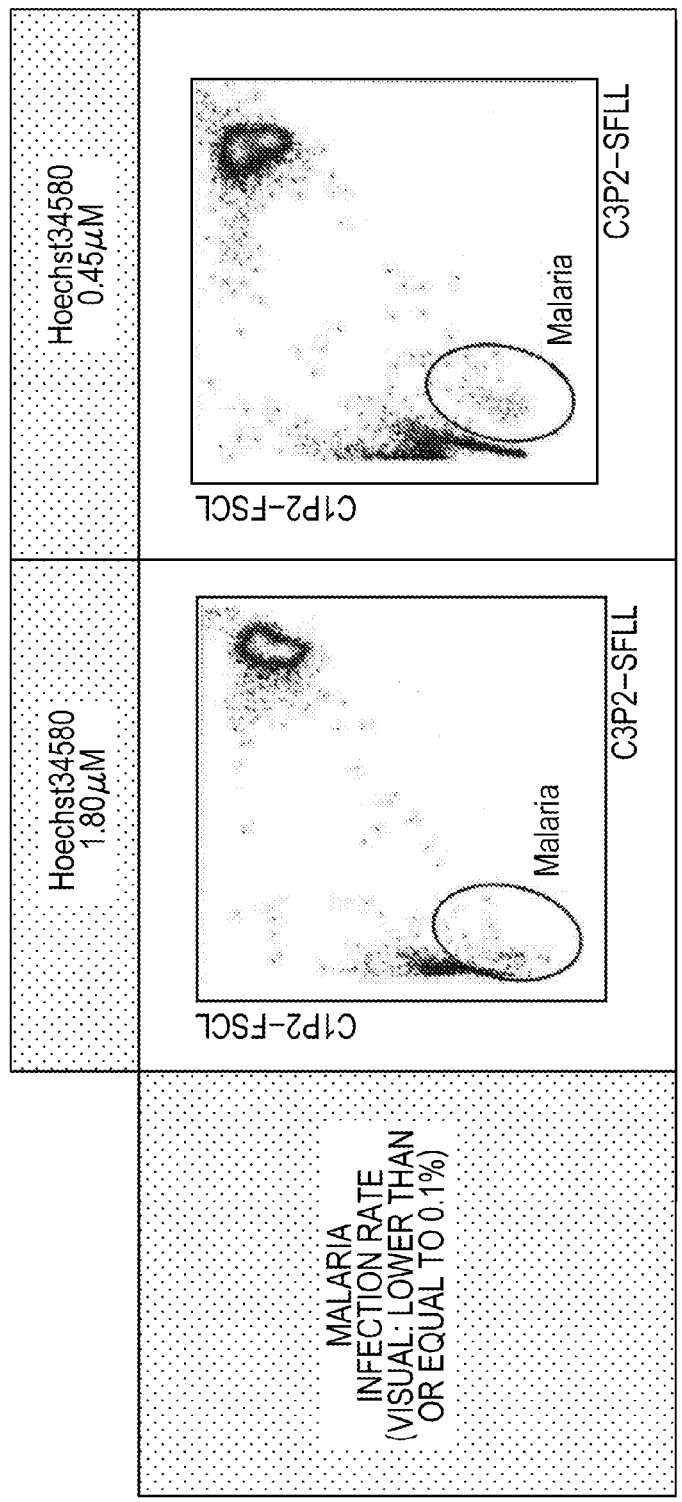
FIG. 16 is a scattergram when a specimen with low malaria infection rate was used.

The result is shown in FIG. 16. As apparent from FIG. 16, the discrimination between the malaria infected red blood cells and the malaria non-infected red blood cells is difficult in 1.80 µM of Hoechst 34580 described in U.S. Patent Application Serial No. 2006/0223137, but the presence of the malaria infected red blood cells can be more clearly confirmed by using the low concentration (0.45 µM) Hoechst 34580.

Comparative Example 2

A stain solution having composition shown in Table 4 below prepared using 4', 6-diamidino-2-phenylindole dihydrochloride (DAPI, Life Technologies) was used in place of Hoechst 34580 to conduct an experiment similar to Example 1.

TABLE 4

|  | DAPI | Ethylene glycol | Concentration in measurement sample |
|---|---|---|---|
| Stain solution 4 | 10 µg | 1 ml | 0.43 µM |
| Stain solution 5 | 20 µg | 1 ml | 0.87 µM |

Figure 17A:
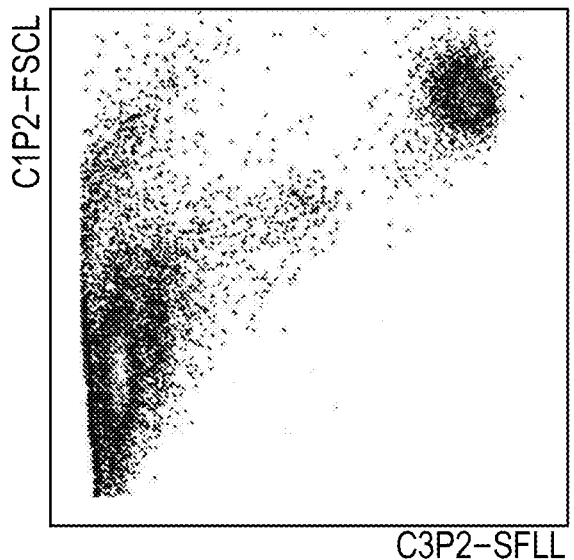
FIG. 17A is a scattergram when DAPI (0.43 µM) was used in place of Hoechst 34580.
Figure 17B:
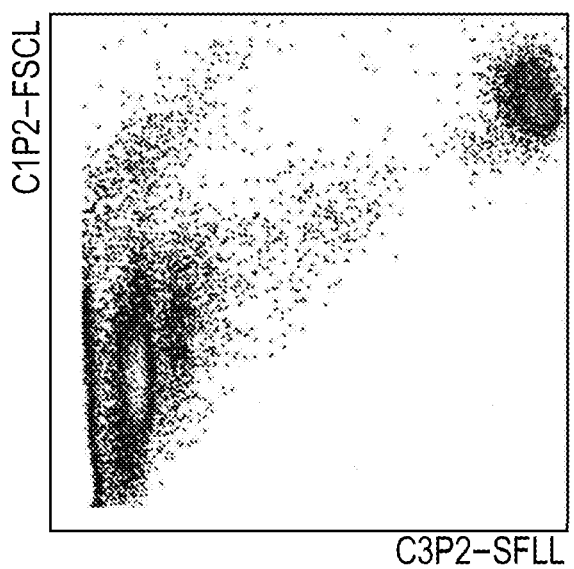
FIG. 17B is a scattergram when DAPI (0.87 µM) was used in place of Hoechst 34580.
Figure 18A:
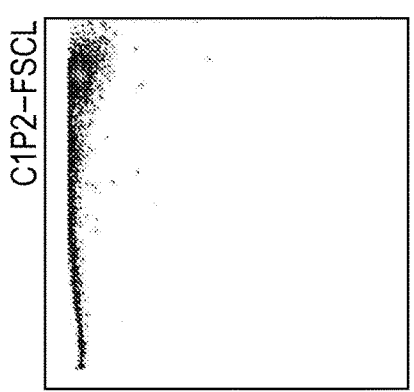
FIG. 18A is a scattergram obtained when the concentration of Hoechst 34580 is 0.00 µM.
Figure 18B:
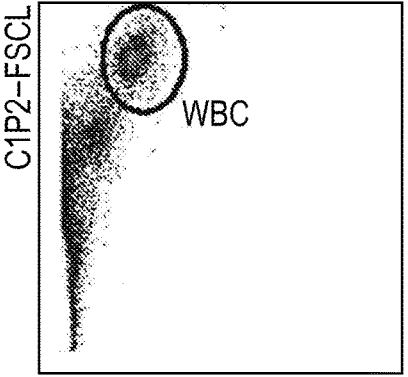
FIG. 18B is a scattergram obtained when the concentration of Hoechst 34580 is 0.02 µM.
Figure 18C:
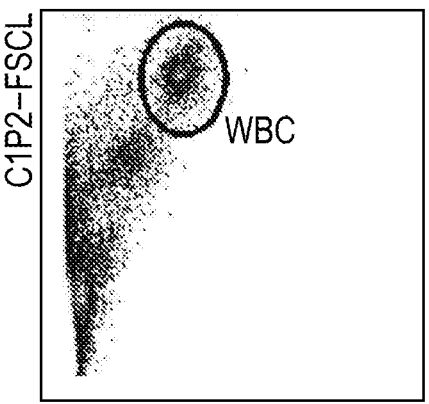
FIG. 18C is a scattergram obtained when the concentration of Hoechst 34580 is 0.04 µM.
Figure 18D:
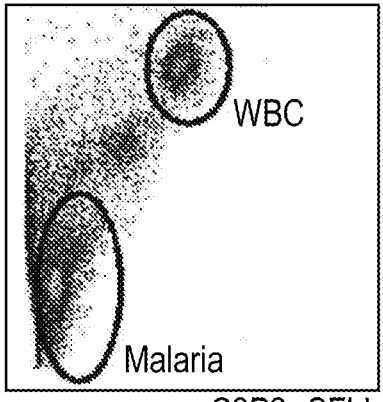
FIG. 18D is a scattergram obtained when the concentration of Hoechst 34580 is 0.07 µM.
Figure 18E:
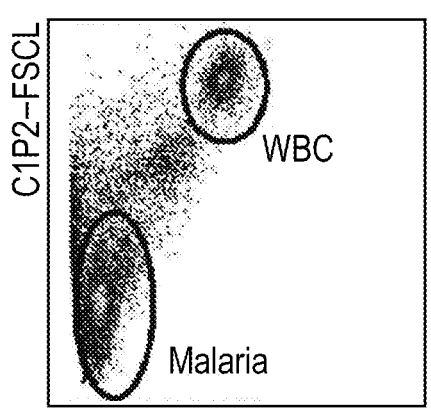
FIG. 18E is a scattergram obtained when the concentration of Hoechst 34580 is 0.09 µM.
Figure 18F:
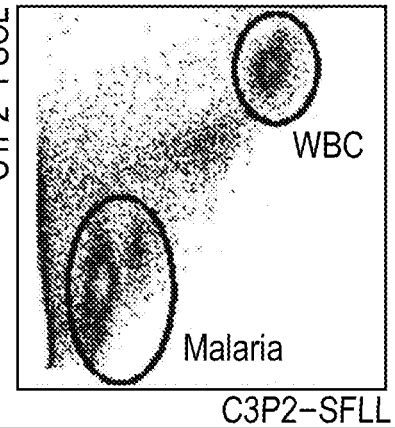
FIG. 18F is a scattergram obtained when the concentration of Hoechst 34580 is 0.18 µM.
Figure 18G:
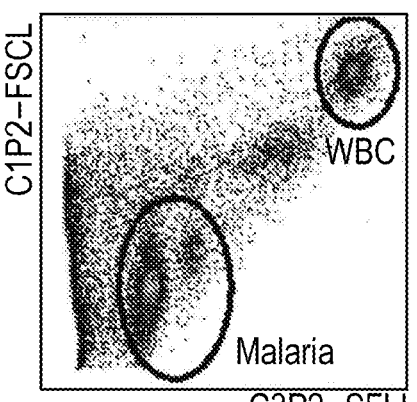
FIG. 18G is a scattergram obtained when the concentration of Hoechst 34580 is 0.36 µM.
Figure 18H:
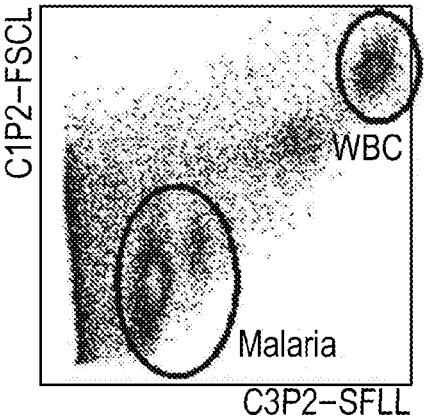
FIG. 18H is a scattergram obtained when the concentration of Hoechst 34580 is 0.45 µM.
Figure 18I:
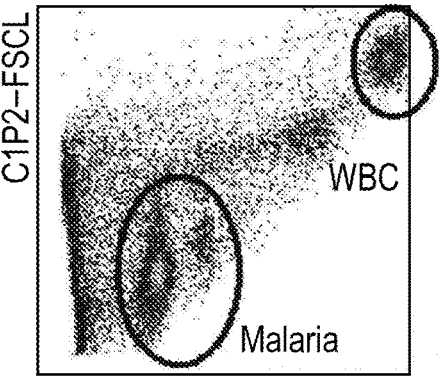
FIG. 18I is a scattergram obtained when the concentration of Hoechst 34580 is 0.62 µM.
Figure 18J:
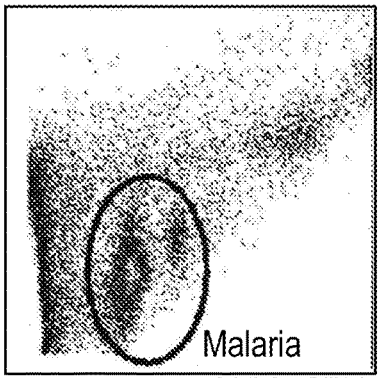
FIG. 18J is a scattergram obtained when the concentration of Hoechst 34580 is 0.89 µM.

The results are shown in FIGS. 17A and 17B. The DAPI is a DNA selective fluorescent dye which is the same as Hoechst 34580, but improvement in separation capacity between the malaria infected red blood cells and the malaria non-infected red blood cells due to lowering of the concentration was not recognized. Thus, it can be seen that the effect of improvement in separation capacity between the malaria infected red blood cells and the malaria non-infected red blood cells due to lowering of the concentration can be recognized when Hoechst 34580 is used at a predetermined concentration.

Example 4

A stain solution having composition shown in Table 5 was used to conduct an experiment similar to Example 1. When the measurement sample was prepared, the stain solution was added so as to realize the value of "concentration in measurement sample" shown on the right column of Table 5.

TABLE 5

|  | HOECHST 34580 | Ethylene glycol | Concentration in measurement sample |
|---|---|---|---|
| Stain solution 3 | 12.5 µg | 1 ml | 0.45 µM |
| Stain solution 6 | 0.5 µg | 1 ml | 0.02 µM |
| Stain solution 7 | 1.0 µg | 1 ml | 0.04 µM |
| Stain solution 8 | 1.85 µg | 1 ml | 0.07 µM |
| Stain solution 9 | 2.5 µg | 1 ml | 0.09 µM |
| Stain solution 10 | 5.0 µg | 1 ml | 0.18 µM |
| Stain solution 11 | 10.0 µg | 1 ml | 0.36 µM |
| Stain solution 12 | 17.5 µg | 1 ml | 0.62 µM |
| Stain solution 13 | 25.0 µg | 1 ml | 0.89 µM |

The results are shown in FIGS. 18A to 18J. It can be seen from FIGS. 18A to 18J that the malaria infected red blood cells and the malaria non-infected red blood cells can be separated at a concentration of 0.18 µM. It can be seen that the fluorescence intensity of white blood cells (WBC) increases and the distribution of white blood cells moves toward the right side of the graph with an increase in concentration of Hoechst 34580 (saturated on the right side of the graph at 0.89 µM). On the other hand, even if the concentration is increased from 0.36 µM, an increase in the fluorescence intensity of the malaria infected red blood cells is low and the distribution hardly moves, whereas the fluorescence intensity of the malaria non-infected red blood cells increases with the increase in concentration, so that the malaria infected red blood cells and the malaria non-infected red blood cells are difficult to be separate when the concentration is excessively increased. The results show that the separation between the malaria infected red blood cells and the malaria non-infected red blood cells is difficult since the fluorescence intensity of the malaria infected red blood cells is not sufficient if the concentration of the fluorescent dye in the measurement sample is too low, and the separation between the malaria infected red blood cells and the malaria non-infected red blood cells is difficult since the fluorescence intensity of the malaria non-infected red blood cells approaches that of the malaria infected red blood cells if the concentration of the fluorescent dye in the measurement sample is too high. Therefore, it is assumed that satisfactory separation between the malaria infected red blood cells and the malaria non-infected red blood cells can be obtained when the concentration of the fluorescent dye in the measurement sample is greater than or equal to 0.15 µM and smaller than or equal to 1.0 µM.

What is claimed is:
1. A blood analyzing method comprising:
preparing a measurement sample from blood, a fluorescent dye represented by the following formula 1, and a diluent, a concentration of the fluorescent dye in the measurement sample being greater than or equal to 0.15 µM and smaller than or equal to 1.0 µM;

acquiring fluorescence information obtained by irradiating the measurement sample with light; and
detecting a red blood cell infected with a malaria parasite in the blood based on the fluorescence information

[Chemical Formula 1]

Formula 1

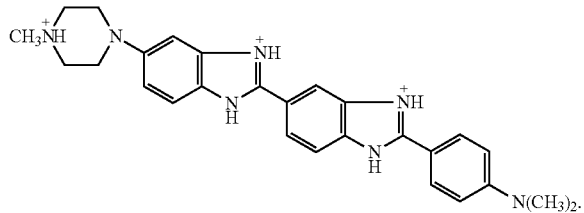

2. The blood analyzing method according to claim 1, wherein the concentration of the fluorescent dye in the measurement sample is greater than or equal to 0.18 µM and smaller than or equal to 0.89 µM.

3. The blood analyzing method according to claim 1, further comprising acquiring forward scattered light information obtained by irradiating the measurement sample with light; wherein
a red blood cell infected with a malaria parasite in the blood is detected further based on the forward scattered light information.

4. The blood analyzing method according to claim 1, wherein a counter ion of the fluorescent dye is a halide ion.

5. The blood analyzing method according to claim 1, wherein the counter ion of the fluorescent dye is $Cl^-$.

6. The blood analyzing method according to claim 1, wherein the diluent comprise at least two types of surfactants having different dissolving powers with respect to a cell membrane of a red blood cell.

7. The blood analyzing method according to claim 1, wherein the diluent has a pH of greater than or equal to 5.0 and smaller than or equal to 7.0.

8. The blood analyzing method according to claim 1, wherein the diluent has an osmotic pressure with respect to the red blood cell of greater than or equal to 200 mOsm/kg·$H_2O$ and smaller than or equal to 300 mOsm/kg·$H_2O$.

* * * * *